(12) United States Patent
Itoh et al.

(10) Patent No.: US 11,236,042 B2
(45) Date of Patent: *Feb. 1, 2022

(54) METHYLMENTHOL DERIVATIVE AND COOL-SENSATION IMPARTER COMPOSITION CONTAINING SAME

(71) Applicant: TAKASAGO INTERNATIONAL CORPORATION, Tokyo (JP)

(72) Inventors: Hisanori Itoh, Kanagawa (JP); Takaji Matsumoto, Kanagawa (JP); Tomoharu Sato, Tokyo (JP); Makoto Harada, Kanagawa (JP); Masaya Otake, Kanagawa (JP); Masashi Otsuka, Kanagawa (JP)

(73) Assignee: TAKASAGO INTERNATIONAL CORPORATION, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 16/476,448

(22) PCT Filed: Jan. 9, 2018

(86) PCT No.: PCT/JP2018/000208
§ 371 (c)(1),
(2) Date: Jul. 8, 2019

(87) PCT Pub. No.: WO2018/131575
PCT Pub. Date: Jul. 19, 2018

(65) Prior Publication Data
US 2020/0024221 A1 Jan. 23, 2020

(30) Foreign Application Priority Data
Jan. 10, 2017 (JP) .............. JP2017-001852

(51) Int. Cl.
| | | |
|---|---|---|
| C07C 233/60 | (2006.01) | |
| C07C 233/61 | (2006.01) | |
| C07C 233/58 | (2006.01) | |
| A23L 27/20 | (2016.01) | |
| A23L 2/56 | (2006.01) | |
| A23G 4/06 | (2006.01) | |
| A23G 3/36 | (2006.01) | |
| A61K 8/42 | (2006.01) | |
| A61Q 11/00 | (2006.01) | |
| A61Q 5/02 | (2006.01) | |

(52) U.S. Cl.
CPC .............. *C07C 233/60* (2013.01); *A23G 3/36* (2013.01); *A23G 4/06* (2013.01); *A23L 2/56* (2013.01); *A23L 27/203* (2016.08); *A23L 27/204* (2016.08); *A61K 8/42* (2013.01); *A61Q 5/02* (2013.01); *A61Q 11/00* (2013.01); *C07C 233/58* (2013.01); *C07C 233/61* (2013.01); *A23V 2002/00* (2013.01); *C07C 2601/14* (2017.05); *C07C 2601/16* (2017.05)

(58) Field of Classification Search
CPC ... C07C 233/60; C07C 233/58; C07C 233/61; C07C 2601/16; C07C 2601/14; A23L 2/56; A23L 27/203; A23L 27/204; A61K 8/42; A23G 3/36; A23G 34/06; A61Q 5/20; A61Q 11/00; A23V 2002/00
See application file for complete search history.

(56) References Cited

U.S. PATENT DOCUMENTS

| | | | |
|---|---|---|---|
| 3,988,482 | A | 10/1976 | Higashiyama et al. |
| 4,038,270 | A | 7/1977 | Higashiyama et al. |
| 4,459,425 | A | 7/1984 | Amano et al. |
| 5,608,119 | A | 3/1997 | Amano et al. |
| 6,780,443 | B1 | 8/2004 | Nakatsu et al. |
| RE44,339 | E | 7/2013 | Galopin et al. |
| 10,494,330 | B2 * | 12/2019 | Itoh .................. C09K 3/00 |
| 2002/0198412 | A1 | 12/2002 | Green et al. |
| 2003/0215532 | A1 | 11/2003 | Nakatsu et al. |
| 2004/0052735 | A1 | 3/2004 | Nakatsu et al. |
| 2005/0222256 | A1 | 10/2005 | Erman et al. |

(Continued)

FOREIGN PATENT DOCUMENTS

| | | |
|---|---|---|
| CN | 1950057 A | 4/2007 |
| JP | 47-16647 A | 9/1972 |

(Continued)

OTHER PUBLICATIONS

G.A. Patani and E.J. LaVoie. "Bioisosterism: A Rational Approach in Drug Design." Chem. Rev. 1996, 96, 3147-3176. (Year: 1996).*

(Continued)

*Primary Examiner* — Michael P Cohen
(74) *Attorney, Agent, or Firm* — Sughrue Mion, PLLC

(57) ABSTRACT

A cooling agent composition includes a methyl menthol derivative represented by the following general formula (1). In the formula (1), a symbol * indicates an asymmetric carbon atom, X represents a hydrogen atom or a substituent, and Y represents an aryl group having 6 to 20 carbon atoms which may have a substituent.

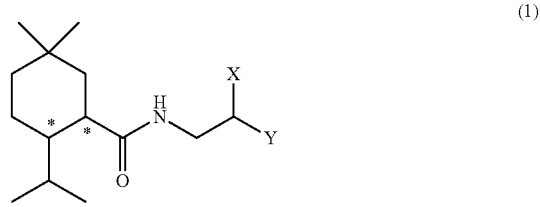

(1)

17 Claims, No Drawings

(56) References Cited

U.S. PATENT DOCUMENTS

| | | |
|---|---|---|
| 2006/0276667 A1 | 12/2006 | Galopin et al. |
| 2007/0225378 A1 | 9/2007 | Ishida et al. |
| 2008/0096969 A1 | 4/2008 | Ley |
| 2008/0300314 A1 | 12/2008 | Galopin et al. |
| 2010/0056636 A1* | 3/2010 | Furrer .................. A24B 15/301 514/617 |
| 2010/0076080 A1 | 3/2010 | Yelm et al. |
| 2011/0015227 A1* | 1/2011 | Desierto ............... A23L 27/203 514/321 |
| 2013/0216486 A1 | 8/2013 | Yelm et al. |
| 2014/0186272 A1 | 7/2014 | Yelm et al. |
| 2018/0057447 A1 | 3/2018 | Itoh et al. |

FOREIGN PATENT DOCUMENTS

| | | |
|---|---|---|
| JP | 47-16648 A | 9/1972 |
| JP | 48-33069 A | 5/1973 |
| JP | 58-88334 A | 5/1983 |
| JP | 61-194049 A | 8/1986 |
| JP | 2-290827 A | 11/1990 |
| JP | 5-255186 A | 10/1993 |
| JP | 5-255217 A | 10/1993 |
| JP | 6-65023 A | 3/1994 |
| JP | 7-82200 A | 3/1995 |
| JP | 7-118119 A | 5/1995 |
| JP | 2001-294546 A | 10/2001 |
| JP | 2005-343915 A | 12/2005 |
| JP | 2007-511546 T | 5/2007 |
| JP | 2007-530689 T | 11/2007 |
| JP | 2008-115181 A | 5/2008 |
| JP | 2010-513657 T | 4/2010 |
| JP | 2011-530608 T | 12/2011 |
| WO | 2005/020897 A2 | 3/2005 |
| WO | 2013/033501 A1 | 3/2013 |
| WO | 2016/153011 A1 | 9/2016 |

OTHER PUBLICATIONS

S. Alankar. A Review on Peppermint Oil. Asian Journal of Pharmaceutical and Clinical Research, vol. 2, Issue 2, Apr.-Jun. 2009, pp. 27-33 (Year: 2009).*

Scifinder Structure Search for monomethyl compound_Dec. 4, 2020 (Year: 2020).*

D.C. Wigfield and D.J. Phelps. The Factors Influencing Stereochemistry in the Reduction of Conformationally Mobile 2-Alkylcyclohexanones by Sodium Borohydride. Journal of the American Chemical Society, 96:2, Jan. 23, 1974, 543-549. (Year: 1974).*

International Search Report (PCT/ISA/210) dated Feb. 13, 2018 by the International Searching Authority in counterpart International Patent Application No. PCT/JP2018/000208.

Written Opinion (PCT/ISA/237) dated Feb. 13, 2018 by the International Searching Authority in counterpart International Patent Application No. PCT/JP2018/000208.

Office Action dated Apr. 6, 2021, issued by the Indonesian Patent Office in corresponding Indonesian Patent Application No. PID201905738.

Communication dated Mar. 18, 2021, from the European Patent Office in European Application No. 18739432.5.

Office Action dated Feb. 9, 2021 by the Intellectual Property Office of India in Indian Patent Application No. 201947027272.

Communication dated Jul. 22, 2020, issued by the European Patent Office in European Application No. 18739432.5.

Communication dated Oct. 8, 2021 by the Indian Patent Office in Indian Patent Application No. 201947027272.

Communication dated Nov. 25, 2021 by China National Intellectual Property Administration in Chinese Patent Application No. 201880006345.4.

* cited by examiner

METHYLMENTHOL DERIVATIVE AND COOL-SENSATION IMPARTER COMPOSITION CONTAINING SAME

TECHNICAL FIELD

The present invention relates to a novel methyl menthol derivative and a cooling agent composition containing the methyl menthol derivative. Further, the present invention relates to a sensory stimulant composition containing the cooling agent composition, and a flavor or fragrance composition and products, each blending with the sensory stimulant composition.

BACKGROUND ART

Up to now, cooling agents which exert a refreshing sense (refresh-feeling) or cool sense (cool-feeling), namely cooling effect, on human skin, oral cavity, nose and throat are used in dentifrices, sweets (e.g., chewing gum, candy, and the like), tobacco, poultice, cosmetics, and the like. As a flavoring substance that provides such a refresh-feeling or cool-feeling, 1-menthol is now broadly used. However, the cooling effect of 1-menthol has a weak point that the cooling effect thereof lacks persistence, and the cooling effect is enhanced when the using amount thereof is increased but bitterness sometimes accompanies.

In addition to 1-menthol, a large number of compounds have been proposed and also used as the compounds having a cooling effect. In exemplifying the so far proposed compounds having a cooling effect other than 1-menthol, 3-substituted-p-menthane (e.g., see PTL 1), N-substituted-p-menthane-3-carboxamide (e.g., see PTL 2 and PTL 3), 1-menthyl glucoside (e.g., see PTL 4), 3-(1-menthoxy)propane-1,2-diol (e.g., see PTL 5), 1-menthyl-3-hydroxybutyrate (e.g., see PTL 6), 1-alkoxy-3-(l-menthoxy)propane-2-ol (e.g., see PTL 7), 3-hydroxymethyl-p-menthane esters (e.g., see PTL 8), N-acetylglycine menthane methyl ester (e.g., see PTL 9), 1-isopulegol (e.g., see PTL 10), (2S)-3-{(1R,2S,5R)-[5-methyl-2-(1-methylethyl)cyclohexyl]oxy}-1,2-propanediol (e.g., see PTL 11), 2-hydroxymethyl menthol (e.g., see PTL 12), menthoxyalkane-1-ol (e.g., see PTL 13), (1-menthyloxy alkoxy)alkanol (e.g., see PTL 14), N-substituted-p-menthane carboxamides (e.g., see PTL 15 and PTL 16), N-α-(menthanecarbonyl)amino acid amide (e.g., see PTL 17), isopulegol derivatives (e.g., see PTL 18), methyl menthol derivatives (e.g., see PTL 19), and the like may be mentioned.

CITATION LIST

Patent Literature

PTL 1: JP S47-16647 A
PTL 2: JP S47-16648 A
PTL 3: JP 2007-530689 A
PTL 4: JP S48-33069 A
PTL 5: JP S58-88334 A
PTL 6: JP S61-194049 A
PTL 7: JP H02-290827 A
PTL 8: JP H05-255186 A
PTL 9: JP H05-255217 A
PTL 10: JP H06-65023 A
PTL 11: JP H07-82200 A
PTL 12: JP H07-118119A
PTL 13: JP 2001-294546 A
PTL 14: JP 2005-343915 A
PTL 15: JP 2007-511546 A
PTL 16: JP 2011-530608 A
PTL 17: JP 2008-115181 A
PTL 18: WO 2013/033501 A1
PTL 19: WO 2016/153011 A1

SUMMARY OF INVENTION

Technical Problem

However, the so far proposed cooling agents described above have a certain level of cooling effect, but are not yet sufficiently satisfactory in terms of persistence of the cooling effect or the like. In addition, a sensory stimulation effect is required to be further improved.

Therefore, an object of the present invention is to provide a novel methyl menthol derivative that does not have an undesirable stimulus feeling, a peculiar smell, bitterness, or the like, and can be used as a cooling agent or sensory stimulant excellent in persistence of a refresh-feeling or cool-feeling.

In addition, another object of the present invention is to provide a cooling agent composition containing the novel methyl menthol derivative, and a sensory stimulant composition containing the cooling agent composition.

Further, still another object of the present invention is to provide a flavor composition or fragrance composition blended with the sensory stimulant composition and products blended with the sensory stimulant composition or the flavor composition or fragrance composition.

Solution to Problem

With the aim of achieving the objects described above, the present inventors have conducted intensive studies and found that a new methyl menthol derivative, which has a specific organic group at the 1-position of the methyl menthol skeleton, has a strong cooling effect and excellent persistence thereof, does not have a bitterness and is useful as a cooling substance and further as a sensory stimulating substance, and have accomplished the invention.

That is, the present invention relates to the following [1] to [19].

[1] A cooling agent composition comprising a methyl menthol derivative represented by the following general formula (1):

[Chem. 1]

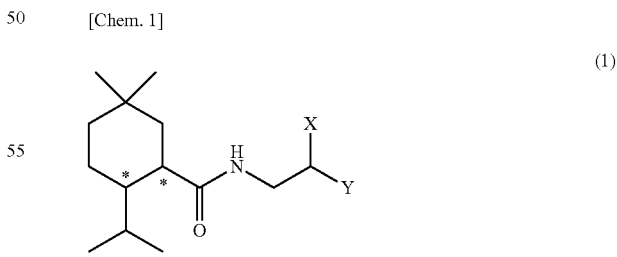

(1)

wherein a symbol * indicates an asymmetric carbon atom, X represents a hydrogen atom or a substituent, and Y represents an aryl group having 6 to 20 carbon atoms which may have a substituent.

[2] The cooling agent composition according to the above [1], wherein X in the general formula (1) represents a hydrogen atom, a hydroxyl group, an acetoxy group, an oxo group, or a methyl group, and Y in the general formula (1) represents a phenyl group which may have a substituent.

[3] The cooling agent composition according to the above [1] or [2], wherein the general formula (1) is represented by the following structural formula (2):

[Chem. 2]

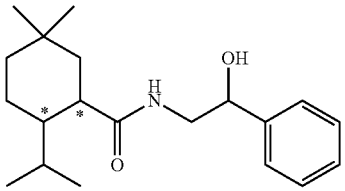

(2)

wherein a symbol * indicates an asymmetric carbon atom.

[4] The cooling agent composition according to any one of the above [1] to [3], further comprising at least one kind of cooling substance other than the methyl menthol derivative.

[5] The cooling agent composition according to the above [4], wherein the cooling substance other than the methyl menthol derivative is at least one cooling substance selected from the group consisting of:

one or more kinds of compounds selected from menthol, menthone, camphor, pulegol, isopulegol, cineole, cubenol, menthyl acetate, pulegyl acetate, isopulegyl acetate, menthyl salicylate, pulegyl salicylate, isopulegyl salicylate, 3-(1-menthoxy)propane-1,2-diol, 2-methyl-3-(1-menthoxy)propane-1,2-diol, 2-(1-menthoxy)ethane-1-ol, 3-(1-menthoxy)propane-1-ol, 4-(1-menthoxy)butan-1-ol, menthyl 3-hydroxybutanoate, menthyl glyoxylate, p-menthane-3,8-diol, 1-(2-hydroxy-4-methylcyclohexyl)ethanone, menthyl lactate, menthone glycerin ketal, menthyl-2-pyrrolidone-5-carboxylate, monomenthyl succinate, alkali metal salts of monomenthyl succinate, alkaline earth metal salts of monomenthyl succinate, monomenthyl glutarate, alkali metal salts of monomenthyl glutarate, alkaline earth metal salts of monomenthyl glutarate, N-{[5-methyl-2-(l-methylethyl)cyclohexyl]carbonyl}glycine, p-menthane-3-carboxylic acid glycerol ester, menthol propylene glycol carbonate, menthol ethylene glycol carbonate, p-menthane-2,3-diol, 2-isopropyl-N,2,3-trimethylbutanamide, N-ethyl-p-menthane-3-carboxamide, 3-(p-menthane-3-carboxamide) ethyl acetate, N-(4-methoxyphenyl)-p-menthane carboxamide, N-ethyl-2,2-diisopropylbutanamide, N-cyclopropyl-p-menthane carboxamide, N-(4-cyanomethylphenyl)-p-menthanecarboxamide, N-(2-pyridin-2-yl)-3-p-menthane carboxamide, N-(2-hydroxyethyl)-2-isopropyl-2,3-dimethylbutanamide, N-(1,1-dimethyl-2-hydroxyethyl)-2,2-diethylbutanamide, cyclopropanecarboxylic acid (2-isopropyl-5-methylcyclohexyl)amide, N-ethyl-2,2-diisopropylbutanamide, N-[4-(2-amino-2-oxoethyl)phenyl]-p-menthanecarboxamide, 2-[(2-p-menthoxy)ethoxy]ethanol, 2,6-diethyl-5-isopropyl-2-methyltetrahydropyran, trans-4-tert-butylcyclohexanol, N-[4-(cyanomethyl)phenyl]-2-isopropyl-5,5-dimethylcyclohexylcarboxamide, and N-[3-hydroxy-4-methoxyphenyl]-2-isopropyl-5,5-dimethylcyclohexylcarboxamide;

one or more kinds of sugar alcohols selected from xylitol, erythritol, dextrose, and sorbitol; and one or more kinds of natural products selected from Japanese mint oil, peppermint oil, spearmint oil, and eucalyptus oil.

[6] A sensory stimulant composition comprising the cooling agent composition according to any one of the above [1] to [5].

[7] The sensory stimulant composition according to the above [6], further comprising at least one kind of warming substance.

[8] The sensory stimulant composition according to the above [7], wherein the warming substance is at least one warming substance selected from the group consisting of:

one or more kinds of compounds selected from vanillyl methyl ether, vanillyl ethyl ether, vanillyl propyl ether, vanillyl isopropyl ether, vanillyl butyl ether, vanillyl amyl ether, vanillyl isoamyl ether, vanillyl hexyl ether, isovanillyl methyl ether, isovanillyl ethyl ether, isovanillyl propyl ether, isovanillyl isopropyl ether, isovanillyl butyl ether, isovanillyl amyl ether, isovanillyl isoamyl ether, isovanillyl hexyl ether, ethyl vanillyl methyl ether, ethyl vanillyl ethyl ether, ethyl vanillyl propyl ether, ethyl vanillyl isopropyl ether, ethyl vanillyl butyl ether, ethyl vanillyl amyl ether, ethyl vanillyl isoamyl ether, ethyl vanillyl hexyl ether, vanillin propylene glycol acetal, isovanillin propylene glycol acetal, ethyl vanillin propylene glycol acetal, vanillyl butyl ether acetate, isovanillyl butyl ether acetate, ethyl vanillyl butyl ether acetate, 4-(1-menthoxymethyl)-2-(3'-methoxy-4'-hydroxyphenyl)-1,3-dioxolane, 4-(1-menthoxymethyl)-2-(3'-hydroxy-4'-methoxyphenyl)-1,3-dioxolane, 4-(1-menthoxymethyl)-2-(3'-ethoxy-4'-hydroxyphenyl)-1,3-dioxolane, capsaicin, dihydrocapsaicin, nordihydrocapsaicin, homodihydrocapsaicin, homocapsaicin, bis-capsaicin, trishomocapsaicin, nomorcapsaicin, norcapsaicin, capsaicinol, vanillyl caprylamide (octylic acid vanillylamide), vanillyl pelargonamide (nonylic acid vanillylamide), vanillyl caproamide (decylic acid vanillylamide), vanillyl undecanamide (undecylic acid vanillylamide), N-trans-feruloyltyramine, N-5-(4-hydroxy-3-methoxyphenyl)-2E,4E-pentadienoylpiperidine, N-trans-feruloylpiperidine, N-5-(4-hydroxy-3-methoxyphenyl)-2E-pentenoylpiperidine, N-5-(4-hydroxyphenyl)-2E,4E-pentadienoylpiperidine, piperine, isopiperine, chavicine, isochavicine, piperamine, piperettine, piperolein B, retrofractamide A, pipercide, guineenside, piperiline, piperamide C5:1 (2E), piperamide C7:1 (6E), piperamide C7:2 (2E,6E), piperamide C9:1 (8E), piperamide C9:2 (2E,8E), piperamide C9:3 (2E,4E,8E), fagaramide, sanshool-I, sanshool-II, hydroxysanshool, sanshoamide, gingerol, shogaol, zingerone, methylgingerol, paradol, spilanthol, chavicine, polygodial (tadeonal), isopolygodial, dihydropolygodial, and tadeon; and one or more kinds of natural products selected from capsicum oil, capsicum oleoresin, ginger oleoresin, jambu oleoresin (Spilanthes oleracea extract), sansho extract, sanshoamide, black pepper extract, white pepper extract, and polygonum extract.

[9] A flavor or fragrance composition comprising the sensory stimulant composition according to any one of the above [6] to [8].

[10] The flavor or fragrance composition according to the above [9], wherein a content of the sensory stimulant composition is from 0.00001 mass % to 90 mass %.

[11] A product comprising the sensory stimulant composition according to any one of the above [6] to [8], the product being any one of products selected from the group consisting of drinks, foods, fragrances or cosmetics, toiletry products, air care products, daily necessities and household goods, oral compositions, hair care products, skin care products, body care products, detergents for clothes, soft finishing agents for clothes, tobacco, quasi-drugs and pharmaceuticals.

[12] The product according to the above [11], wherein a content of the sensory stimulant composition is from 0.00001 mass % to 50 mass %.

[13] A product comprising the flavor or fragrance composition according to the above [9] or [10], the product being any one of products selected from the group consisting of drinks, foods, fragrances or cosmetics, toiletry products, air care products, daily necessities and household goods, oral compositions, hair care products, skin care products, body care products, detergents for clothes, soft finishing agents for clothes, tobacco, quasi-drugs and pharmaceuticals.

[14] The product according to the above [13], wherein a content of the flavor or fragrance composition is from 0.00001 mass % to 50 mass %.

[15] A method of manufacturing a product, comprising blending a product with the sensory stimulant composition according to any one of the above [6] to [8], wherein the product is any one of products selected from the group consisting of drinks, foods, fragrances or cosmetics, toiletry products, air care products, daily necessities and household goods, oral compositions, hair care products, skin care products, body care products, detergents for clothes, soft finishing agents for clothes, tobacco, quasi-drugs and pharmaceuticals.

[16] A method of manufacturing a product, comprising blending a product with the flavor or fragrance composition according to the above [9] or [10], wherein the product is any one of products selected from the group consisting of drinks, foods, fragrances or cosmetics, toiletry products, air care products, daily necessities and household goods, oral compositions, hair care products, skin care products, body care products, detergents for clothes, soft finishing agents for clothes, tobacco, quasi-drugs and pharmaceuticals.

[17] A methyl menthol derivative represented by the following general formula (1):

[Chem. 3]

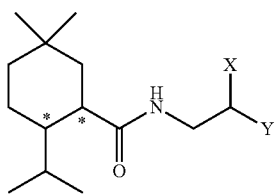

(1)

wherein a symbol * indicates an asymmetric carbon atom, X represents a hydrogen atom or a substituent, and Y represents an aryl group having 6 to 20 carbon atoms which may have a substituent.

[18] The methyl menthol derivative according to the above [17], wherein X in the general formula (1) represents a hydrogen atom, a hydroxyl group, an acetoxy group, an oxo group, or a methyl group, and Y in the general formula (1) represents a phenyl group which may have a substituent.

[19] The methyl menthol derivative according to the above [17] or [18], wherein the general formula (1) is represented by the following structural formula (2):

[Chem. 4]

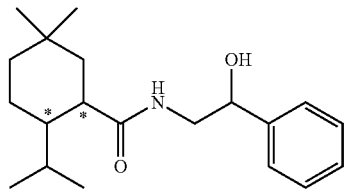

(2)

wherein a symbol * indicates an asymmetric carbon atom.

Advantageous Effects of Invention

The cooling agent composition containing the methyl menthol derivative of the present invention is strong in the cooling intensity, and has a clear cool-feeling. In addition, the cooling agent composition is excellent in the persistence of the cooling effect, and is less bitter. Therefore, the cooling agent composition of the present invention is blended with various products, so that a refresh-feeling or cool-feeling excellent in the persistence can be given to these products.

DESCRIPTION OF EMBODIMENTS

Hereinafter, the present invention is described in detail, but the present invention is not limited to the following embodiments, and may be arbitrarily modified and implemented without departing from the scope of the present invention. In addition, the "compound represented by the formula (X)" is sometimes simply referred to as "compound (X)" in the present description.

In addition, "weight %" and "mass %" have the same definition in the present description. In addition, when a unit "ppm" is described, it denotes "weight ppm". Further, the expression "to" showing a numerical range is used to include the numerical value described therebefore as the lower limit and the numerical value described thereafter as the upper limit.

A cooling agent composition of the invention contains a methyl menthol derivative represented by the following general formula (1) as a cooling substance.

[Chem. 5]

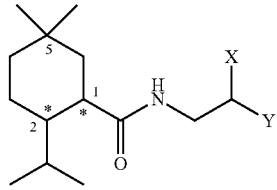

(1)

[In the formula (1), a symbol * indicates an asymmetric carbon atom, X represents a hydrogen atom or a substituent, and Y represents an aryl group having 6 to 20 carbon atoms which may have a substituent.]

Specifically, the methyl menthol derivative represented by the general formula (1) has a cyclohexane ring structure, and has asymmetric carbon atoms at the 1-position and 2-position. Therefore, four diastereomers represented by the following formulas (1-a) to (1-d) exist.

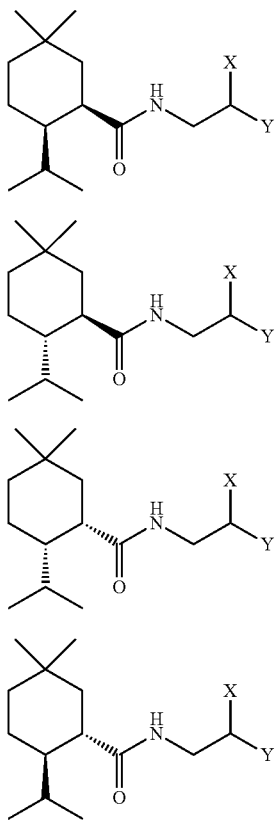

(1-a)
(1-b)
(1-c)
(1-d)

The methyl menthol derivative represented by the general formula (1) is preferably the trans form.

In the general formula (1), X represents a hydrogen atom or a substituent.

As the substituent, examples thereof include a hydroxyl group, an acetoxy group, an oxo group, an alkyl group having 1 to 10 carbon atoms, a hydroxymethyl group, a hydroxyethyl group, a methoxy group, an ethoxy group, a phenoxy group, and the like. As the alkyl group having 1 to 10 carbon atoms, examples thereof include a methyl group, an ethyl group, a n-propyl group, an isopropyl group, an isobutyl group, a sec-butyl group, a tert-butyl group, a pentyl group, a hexyl group, a heptyl group, an octyl group, a nonyl group, a decyl group, and the like.

Among the above examples of X, X is preferably a hydrogen atom, a hydroxyl group, an acetoxy group, an oxo group, or a methyl group, from the viewpoint of cooling persistence, cooling intensity, less bitterness, and manufacturing easiness.

In the general formula (1), Y represents an aryl group having 6 to 20 carbon atoms which may have a substituent.

As the aryl group having 6 to 20 carbon atoms, a monocyclic aromatic group, a polycyclic aromatic group, or a fused-ring aromatic group, which have 6 to 20 carbon atoms, may be mentioned. Specific examples thereof include a phenyl group, a naphthyl group, an anthryl group, a phenanthryl group, and an indenyl group.

Examples of the substituent which may be contained in the aryl group having 6 to 20 carbon atoms include: a hydroxyl group; a hydroxyalkyl group having 1 to 4 carbon atoms such as a hydroxymethyl group, a hydroxyethyl group, a 2-hydroxyethyl group, a 1-hydroxypropyl group, a 2-hydroxypropyl group, and a 1-hydroxybutyl group; an alkoxy group having 1 to 6 carbon atoms such as a methoxy group, an ethoxy group, a n-propoxy group, an isopropoxy group, a n-butoxy group, an isobutoxy group, a sec-butoxy group, a methylenedioxy group, an ethylenedioxy group, a tert-butoxy group, and a phenoxy group; a mercapto group; a thioalkoxy group having 1 to 4 carbon atoms such as a thiomethoxy group, a thioethoxy group, a n-thiopropoxy group, a thioisopropoxy group, a n-thiobutoxy group, a thioisobutoxy group, a sec-thiobutoxy group, a methylene dithio group, and a tert-thiobutoxy group; an alkyl group having 1 to 6 carbon atoms such as a methyl group, an ethyl group, a n-propyl group, an isopropyl group, a n-butyl group, an isobutyl group, a sec-butyl group, a tert-butyl group, a pentyl group, and a hexyl group; a cycloalkyl group having 5 to 8 carbon atoms such as a cyclopentyl group, a cyclohexyl group, and a cycloheptyl group; a halogen atom such as a fluorine atom, a chlorine atom, a bromine atom, and an iodine atom; a phenyl group; an aralkyl group having 7 to 12 carbon atoms such as a benzyl group, a phenylethyl group, and a naphthylmethyl group; a carboxy group; an alkoxycarbonyl group having 2 to 8 carbon atoms such as a methoxy carbonyl group, an ethoxycarbonyl group, and a benzyloxycarbonyl group; an acyl group having 1 to 7 carbon atoms such as a formyl group, an acetyl group, a propionyl group, and a benzoyl group; a carboxamide group; a dialkylamino group having 2 to 8 carbon atoms such as a dimethylamino group, a diethylamino group, and a dibutylamino group; a nitrile group; a cyanoalkyl group (the alkyl group therein having 1 to 4 carbon atoms) such as a cyanomethyl group, a cyanoethyl group, a cyanopropyl group, and a cyanobutyl group; an aliphatic heterocyclic group such as an oxiranyl group, an aziridinyl group, a 2-oxopyropidyl group, a piperidyl group, a piperazinyl group, a morpholino group, a tetrahydrofuryl group, a tetrahydropyranyl group, and a tetrahydrothienyl group; and an aromatic heterocyclic group such as a tetrazinyl group, a furyl group, a thienyl group, a pyridyl group, a pyridinyl group, a pyrazinyl group, a pyradazinyl group, an imidazoyl group, an oxazoyl group, a thiazoyl group, a benzofuryl group, a benzothienyl group, a quinolyl group, an isoquinolyl group, a quinoxanoyl group, a phthalazinyl group, a quinazolinyl group, a naphthyldinyl group, a cinnolinyl group, a benzimidazoline group, a benzoxazolyl group, and a benzothiazolyl group.

In the present invention, Y is preferably a phenyl group which may have a substituent, from the viewpoint of cooling persistence, cooling intensity, less bitterness, and manufacturing easiness.

The methyl menthol derivative (1) of the present invention is synthesized, for example, by the methods represented by the following schemes 1 to 5. However, the synthesis method thereof is not limited to the methods of the following schemes 1 to 5.

The methyl menthol derivative (1) of the present invention is synthesized from a ketone compound represented by the following formula (3) (hereinafter, referred to as ketone compound (3)) or an alcohol compound represented by the following formula (4) (hereinafter, referred to as alcohol compound (4)), according to the method described in WO 2016/153011 A1. Further, in the following formulas (3) and (4), a symbol * indicates an asymmetric carbon atom.

[Chem. 7]

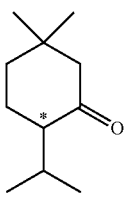
(3)

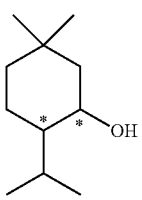
(4)

The ketone compound (3) and the alcohol compound (4) are synthesized according to the method shown in the following scheme 1.

(In the above scheme 1, a symbol * indicates an asymmetric carbon atom.)

Steps [A], [B], and [D] can be performed in a manner similar to that described in Tetrahedron 1986, Vol. 42, No. 8, p2230. That is, Step [A] can be performed by a conjugate addition (1,4-addition) reaction, Step [B] can be performed by an intramolecular prins reaction, and Step [D] can be performed by a conjugate addition (1,4-addition) reaction. In addition, Step [C] can be performed by hydrogenation using a commonly used metal catalyst such as nickel or palladium. Step [E] can be performed in a manner similar to that described in J. Mol. Cat. A (1996), No. 109, PP. 201-208, that is, a hydrogenation reaction.

Next, for example, a carboxylic acid compound represented by the following general formula (11) (hereinafter, also referred to as "carboxylic acid compound (11)") is synthesized from the ketone compound (3) or the alcohol compound (4) according to the method shown in the following scheme 2.

Meanwhile, an aldehyde compound represented by the general formula (13) (hereinafter, also referred to as "aldehyde compound (13)") is synthesized from the ketone compound (3), for example, according to the method shown in the following scheme 2.

[Scheme 1]

[Chem. 8]

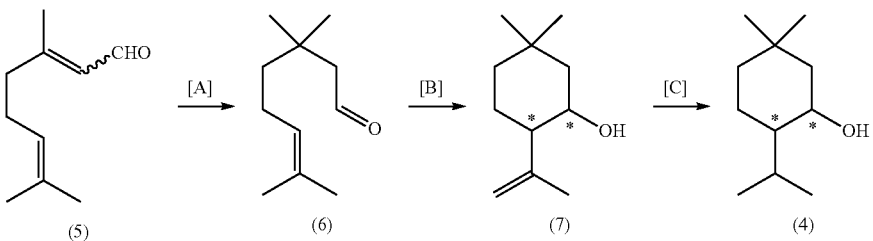

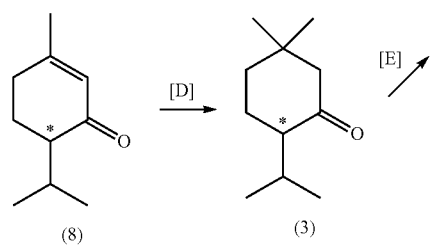

[Scheme 2]

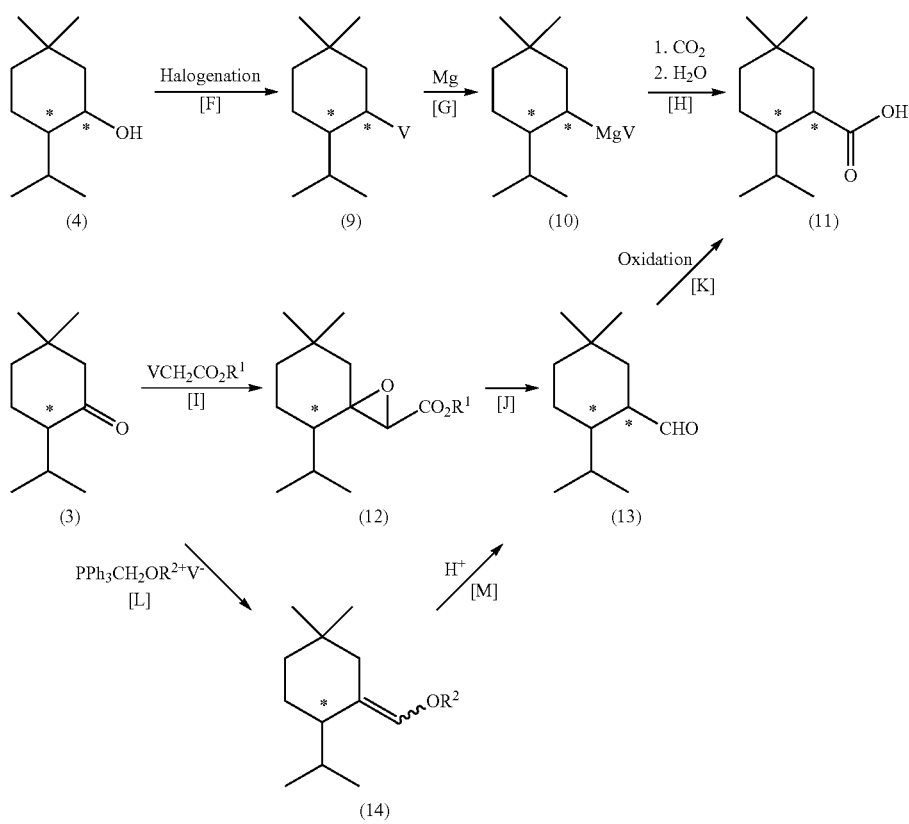

(In the above scheme 2, a symbol * indicates an asymmetric carbon atom, $R^1$ and $R^2$ represent a linear or branched alkyl group having 1 to 10 carbon atoms which may have a substituent, V represents a halogen atom, and Ph represents a phenyl group.)

In the halogenation reaction of Step [F], for example, the halide (9) (V=Cl) can be synthesized by allowing the alcohol compound (4) to react with phosphorus pentachloride. In addition, Step [F] can also be performed in a manner similar to that described in J. Chem. Soc. Perkin Trans., (1990):pp. 1275 to 1277. Steps [G] and [H] can be performed in a manner similar to those described in British Patent Application Publication No. 1392907. Steps [I], [J] and [K] can be performed in a manner similar to those described in German Patent Application Publication No. 102012202885. Steps [L] and [M] can be performed in a manner similar to those described in J. Am. Chem. Soc. (2004), Vol. 126, No. 41, pp. 13312-13319.

The compound represented by the general formula (1) of the present invention can be synthesized from the carboxylic acid compound (11) obtained by the above method, for example, according to the method shown in the following scheme 3.

[Scheme 3]

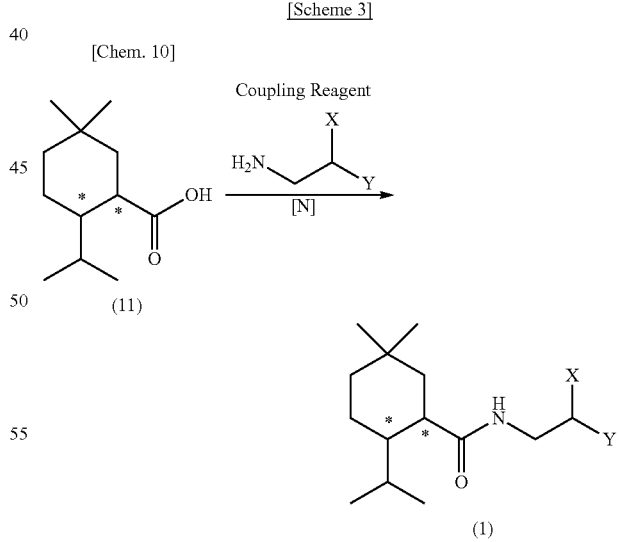

(A symbol *, X, and Y in the above scheme 3 have the same definitions as those in the above schemes.)

In the case of synthesizing the compound according to the scheme 3, Step [N] can be performed in a manner similar to that of WO 2013/033501 A1.

Alternatively, the compound represented by the general formula (1) of the present invention can be synthesized from the carboxylic acid compound (11), for example, according to the method shown in the following scheme 4.

[Scheme 4]

[Chem. 11]

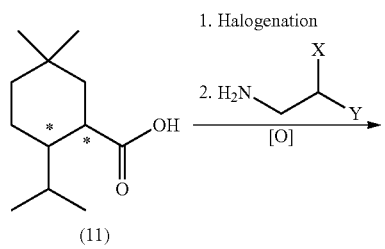

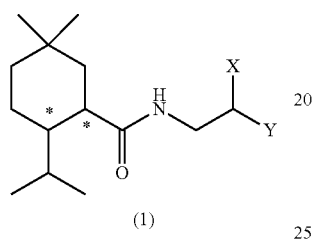

(A symbol *, X, and Y in the above scheme 4 have the same definitions as those in the above schemes.)

In the case of synthesizing the compound according to the scheme 4, Step [O] can be performed in a manner similar to that of JP S47-16648 A or WO 2013/033501 A1.

Further, the compound represented by the general formula (1) of the present invention can also be synthesized from the carboxylic acid compound (11), for example, according to the method shown in the following scheme 5.

[Scheme 5]

[Chem. 12]

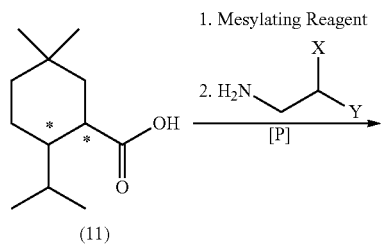

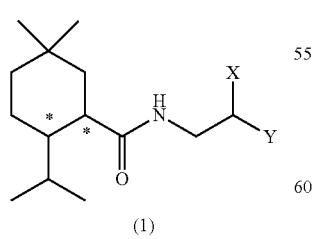

(A symbol *, X, and Y in the above scheme 5 have the same definitions as those in the above schemes.)

In the case of synthesizing the compound according to the scheme 5, Step [P] can be performed by mesylating the carboxylic acid compound (11) to convert it to an active acyl intermediate thereof, and then allowing the active acyl intermediate to react with an amine.

The following compounds may be mentioned as preferred specific examples of the methyl menthol derivative of the present invention represented by the formula (1), but the methyl menthol derivative is not limited to these compounds.

In the following compounds, Me represents a methyl group, Et represents an ethyl group, and Ac represents an acetyl group.

[Chem. 13]

(1-1)

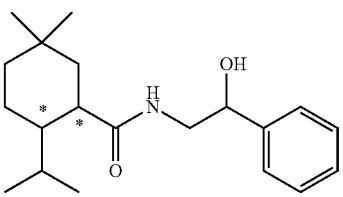 [SMILES: CC(C)C1CCC(C)(C)CC1C(=O)NCC(O)c1ccccc1]

(1-2)

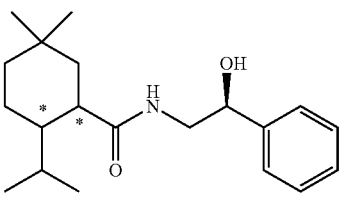

(1-3)

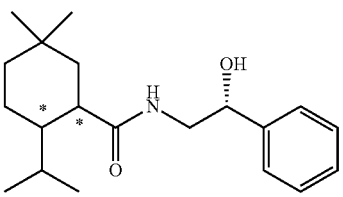 [SMILES: CC(C)C1CCC(C)(C)CC1C(=O)NC[C@H](O)c1ccccc1]

(1-4)

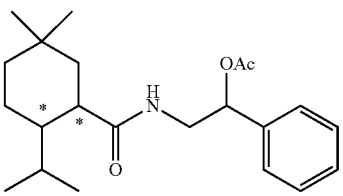 [SMILES: CC(=O)OC(CNC(=O)C1CC(C)(C)CCC1C(C)C)c1ccccc1]

(1-5)

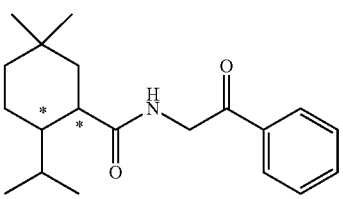 [SMILES: CC(C)C1CCC(C)(C)CC1C(=O)NCC(=O)c1ccccc1]

(1-6)

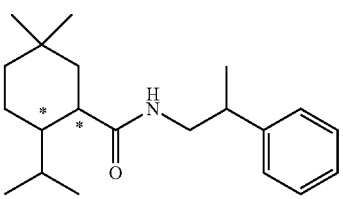 [SMILES: CC(CNC(=O)C1CC(C)(C)CCC1C(C)C)c1ccccc1]

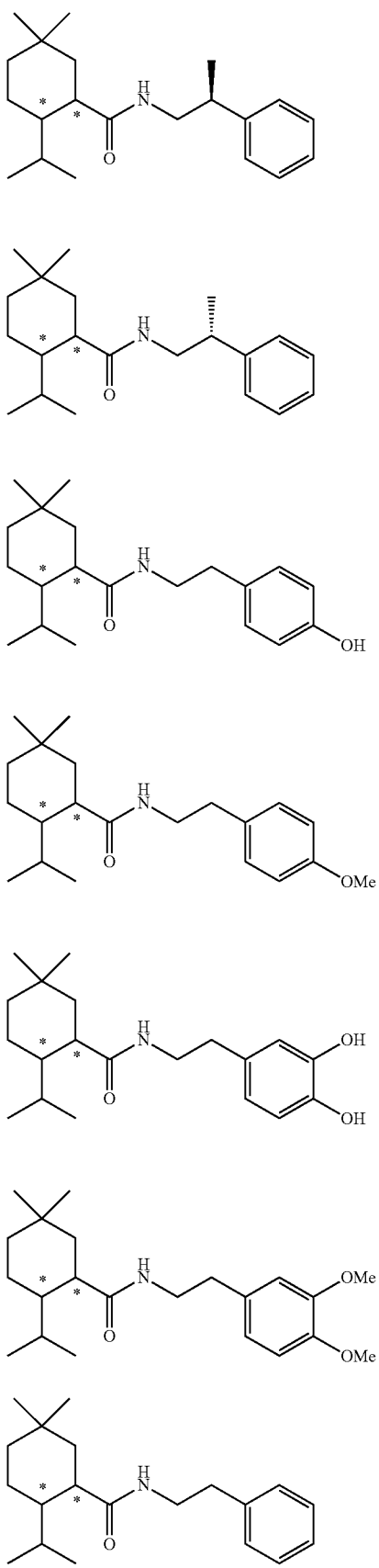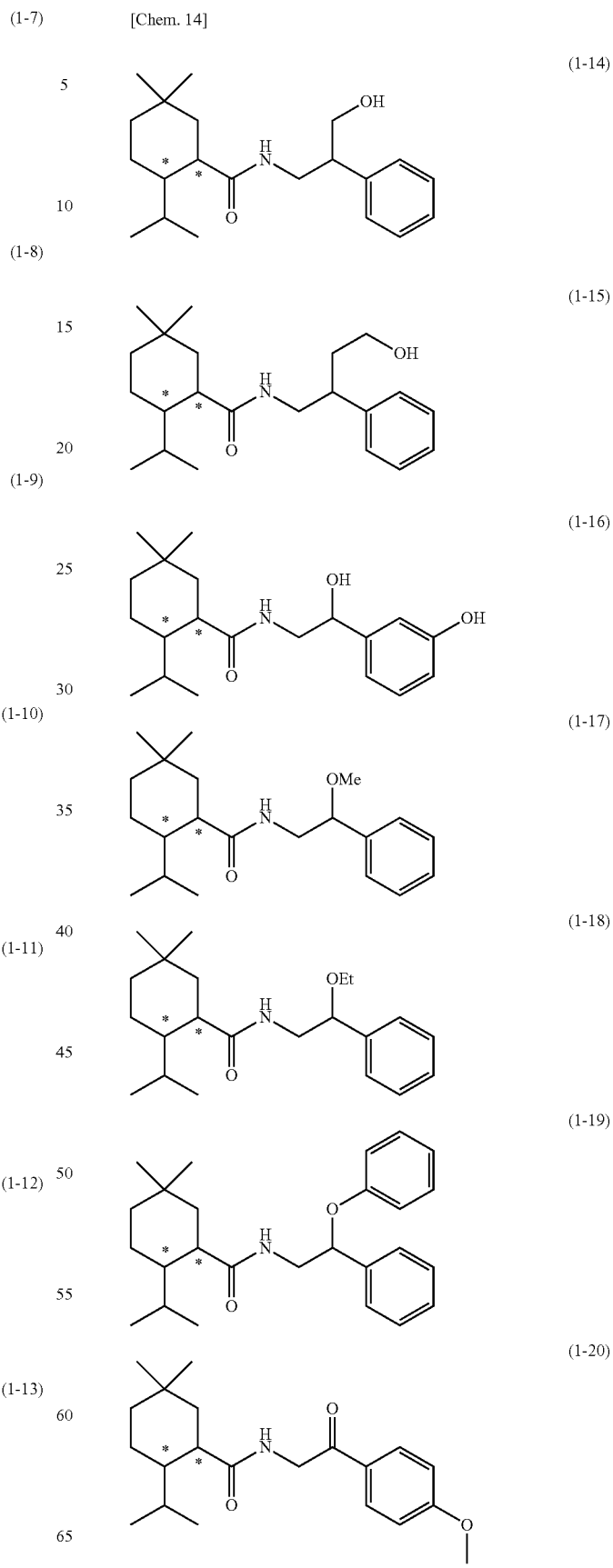

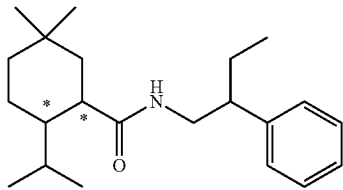
(1-21)

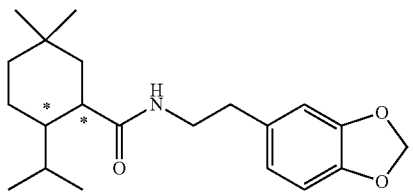
(1-22)

The methyl menthol derivative represented by the general formula (1) of the present invention and obtained in this manner can have a strong and persistent cooling effect, and can be used alone as a cooling agent or a sensory stimulant.

The application range and the application method of the methyl menthol derivative of the present invention are required to be appropriately changed depending on the kinds of products and application purposes. However, the methyl menthol derivative of the present invention is generally used at a concentration of $1.0 \times 10^{-8}$ mass % to 50 mass %, preferably $1.0 \times 10^{-7}$ mass % to 20 mass %, and particularly preferably $1.0 \times 10^{-6}$ mass % to 5 mass %, based on the total composition of the products.

In the case of preparing a cooling agent composition, the application range and the application method of the methyl menthol derivative content are required to be appropriately changed depending on the kinds of products and application purposes. However, the content thereof is generally 0.00001 mass % to 100 mass %, preferably 0.0001 mass % to 50 mass %, and particularly preferably 0.001 mass % to 30 mass %, based on the total mass of the cooling agent composition.

In the cooling agent composition containing the methyl menthol derivative in the present invention, at least one kind of cooling substance other than the methyl menthol derivative of the present invention is used in combination with the methyl menthol derivative of the present invention, so that a cooling agent composition having an increased cooling intensity can be obtained.

Further, a sensory stimulant composition containing the cooling agent composition with an increased cooling intensity can be prepared.

Examples of the cooling substance that does not fall within the methyl menthol derivative of the invention include:

compounds (α) such as menthol, menthone, camphor, pulegol, isopulegol, cineole, cubenol, menthyl acetate, pulegyl acetate, isopulegyl acetate, menthyl salicylate, pulegyl salicylate, isopulegyl salicylate, 3-(1-menthoxy)propane-1,2-diol, 2-methyl-3-(1-menthoxy)propane-1,2-diol, 2-(1-menthoxy)ethane-1-ol, 3-(1-menthoxy)propane-1-ol, 4-(1-menthoxy)butan-1-ol, menthyl 3-hydroxybutanoate, menthyl glyoxylate, p-menthane-3,8-diol, 1-(2-hydroxy-4-methylcyclohexyl)ethanone, menthyl lactate, menthone glycerin ketal, menthyl-2-pyrrolidone-5-carboxylate, monomenthyl succinate, alkali metal salts of monomenthyl succinate, alkaline earth metal salts of monomenthyl succinate, monomenthyl glutarate, alkali metal salts of monomenthyl glutarate, alkaline earth metal salts of monomenthyl glutarate, N-{[5-methyl-2-(1-methylethyl)cyclohexyl]carbonyl}) glycine, p-menthane-3-carboxylic acid glycerol ester, menthol propylene glycol carbonate, menthol ethylene glycol carbonate, p-menthane-2,3-diol, 2-isopropyl-N,2,3-trimethylbutanamide, N-ethyl-p-menthane-3-carboxamide, 3-(p-menthane-3-carboxamide) ethyl acetate, N-(4-methoxyphenyl)-p-menthane carboxamide, N-ethyl-2,2-diisopropylbutanamide, N-cyclopropyl-p-menthane carboxamide, N-(4-cyanomethylphenyl)-p-menthanecarboxamide, N-(2-pyridin-2-yl)-3-p-menthane carboxamide, N-(2-hydroxyethyl)-2-isopropyl-2,3-dimethylbutanamide, N-(1,1-dimethyl-2-hydroxyethyl)-2,2-diethylbutanamide, cyclopropanecarboxylic acid (2-isopropyl-5-methylcyclohexyl) amide, N-ethyl-2,2-diisopropylbutanamide, N-[4-(2-amino-2-oxoethyl)phenyl]-p-menthanecarboxamide, 2-[(2-p-menthoxy)ethoxy]ethanol, 2,6-diethyl-5-isopropyl-2-methyltetrahydropyran, trans-4-tert-butylcyclohexanol, N-[4-(cyanomethyl)phenyl]-2-isopropyl-5,5-dimethylcyclohexylcarboxamide, and N-[3-hydroxy-4-methoxyphenyl]-2-isopropyl-5,5-dimethylcyclohexylcarboxamide, and racemic and optically active forms thereof;

sugar alcohols (β) such as xylitol, erythritol, dextrose, and sorbitol;

natural products (γ) such as Japanese mint oil, peppermint oil, spearmint oil, and eucalyptus oil; and compounds (δ) described in JP 2001-294546 A, JP 2005-343915 A, JP 2007-002005 A, JP 2009-263664 A, JP 2010-254621 A, JP 2010-254622 A, JP 2011-079953 A, U.S. Pat. Nos. 4,136,163 A, 4,150,052 A, 4,178,459 A, 4,190,643 A, 4,193,936 A, 4,226,988 A, 4,230,688 A, 4,032,661 A, 4,153,679 A, 4,296,255 A, 4,459,425 A, 5,009,893 A, 5,266,592 A, 5,698,181 A, 5,725,865 A, 5,843,466 A, 6,231,900 B1, 6,277,385 B1, 6,280,762 B1, 6,306,429 B1, 6,432,441 B1, 6,455,080 B1, 6,627,233 B1, 7,078,066 B2, 6,783,783 B2, 6,884,906 B2, 7,030,273 B1, U.S. Pat. No. 7,090,832 B2, US 2004/0175489 A1, US 2004/0191402 A1, US 2005/0019445 A1, US 2005/0222256 A1, US 2005/0265930 A1, US 2006/015819 A1, US 2006/0249167 A1, EP-A 1-1689256, WO 2005/082154 A1, WO 2005/099473 A1, WO 2006/058600 A1, WO 2006/092076 A1, WO 2006/125334 A1, and WO 2016/153011 A1.

These may be used alone or by blending two or more of them. It is preferable that at least one cooling substance selected from the group consisting of the compounds (α), the sugar alcohols (β), and the natural products (γ) is contained.

The methyl menthol derivative of the present invention and the cooling substance not falling within this may be used in any ratio within a range that does not impair effects of the present invention. However, the preferred usage ratio of the methyl menthol derivative to the cooling substance not falling within this is preferably in a range of 1:99 to 90:10 in terms of mass ratio.

The cooling agent composition of the present invention may be blended with a flavor composition or a fragrance composition (hereinafter, referred to as a flavor or fragrance composition), or products such as drinks, foods, fragrances or cosmetics, toiletry products, air care products, daily necessities and household goods, oral compositions, hair care products, skin care products, body care products, detergents for clothes, soft finishing agents for clothes, tobacco, quasi-drugs, and pharmaceuticals.

In addition, the cooling agent composition containing the methyl menthol derivative of the present invention has a strong and persistent cooling effect, and therefore, a sensory stimulant composition having a cooling effect can be prepared by incorporating the cooling agent composition thereto.

In the case of preparing the sensory stimulant composition, the application range and the application method of the blending amount of the cooling agent composition are required to be appropriately changed depending on the kinds of products and application purposes. However, the blending amount thereof is generally from 0.00001 mass % to 50 mass %, preferably from 0.0001 mass % to 20 mass %, and particularly preferably from 0.001 mass % to 4 mass %, based on the total composition of the sensory stimulant composition. The sensory stimulant composition of the present invention is a composition that imparts an effect of stimulating sensation. Examples of the effect of stimulating the sensation include a cooling effect and/or a warming effect. Accordingly, in the present invention, the sensory stimulant composition is described as a concept also including a cooling agent composition and/or a warming agent composition.

The stimulation effect of the sensory stimulant composition can be adjusted by using a warming substance in combination with the cooling agent composition of the present invention. Examples of the warming substance include:

compounds (c) such as vanillyl methyl ether, vanillyl ethyl ether, vanillyl propyl ether, vanillyl isopropyl ether, vanillyl butyl ether, vanillyl amyl ether, vanillyl isoamyl ether, vanillyl hexyl ether, isovanillyl methyl ether, isovanillyl ethyl ether, isovanillyl propyl ether, isovanillyl isopropyl ether, isovanillyl butyl ether, isovanillyl amyl ether, isovanillyl isoamyl ether, isovanillyl hexyl ether, ethyl vanillyl methyl ether, ethyl vanillyl ethyl ether, ethyl vanillyl propyl ether, ethyl vanillyl isopropyl ether, ethyl vanillyl butyl ether, ethyl vanillyl amyl ether, ethyl vanillyl isoamyl ether, ethyl vanillyl hexyl ether, vanillin propylene glycol acetal, isovanillin propylene glycol acetal, ethyl vanillin propylene glycol acetal, vanillyl butyl ether acetate, isovanillyl butyl ether acetate, ethyl vanillyl butyl ether acetate, 4-(1-menthoxymethyl)-2-(3'-methoxy-4'-hydroxyphenyl)-1,3-dioxolane, 4-(l-menthoxymethyl)-2-(3'-hydroxy-4'-methoxyphenyl)-1,3-dioxolane, 4-(1-menthoxymethyl)-2-(3'-ethoxy-4'-hydroxyphenyl)-1,3-dioxolane, capsaicin, dihydrocapsaicin, nordihydrocapsaicin, homodihydrocapsaicin, homocapsaicin, biscapsaicin, trishomocapsaicin, nor-norcapsaicin, norcapsaicin, capsaicinol, vanillyl caprylamide (octylic acid vanillylamide), vanillyl pelargonamide (nonylic acid vanillylamide), vanillyl caproamide (decylic acid vanillylamide), vanillyl undecanamide (undecylic acid vanillylamide), N-trans-feruloyltyramine, N-5-(4-hydroxy-3-methoxyphenyl)-2E,4E-pentadienoylpiperidine, N-trans-feruloylpiperidine, N-5-(4-hydroxy-3-methoxyphenyl)-2E-pentenoylpiperidine, N-5-(4-hydroxyphenyl)-2E,4E-pentadienoylpiperidine, piperine, isopiperine, chavicine, isochavicine, piperamine, piperettine, piperolein B, retrofractamide A, pipercide, guineenside, piperiline, piperamide C5:1 (2E), piperamide C7:1 (6E), piperamide C7:2 (2E,6E), piperamide C9:1 (8E), piperamide C9:2 (2E,8E), piperamide C9:3 (2E,4E,8E), fagaramide, sanshool-I, sanshool-II, hydroxysanshool, sanshoamide, gingerol, shogaol, zingerone, methylgingerol, paradol, spilanthol, chavicine, polygodial (tadeonal), isopolygodial, dihydropolygodial, and tadeon, and racemic and optically active forms thereof, natural products (C) such as capsicum oil, capsicum oleoresin, ginger oleoresin, jambu oleoresin (*Spilanthes oleracea* extract), sansho extract, sanshoamide, black pepper extract, white pepper extract, and polygonum extract; and compounds (11) described in JP H08-225564 A, JP 2007-015953 A, JP 2007-510634 A, JP 2008-505868 A, WO 2007/013811 A1, WO 2003/106404 A1, EP 1323356 A2, DE 10351422 A1, US 2005/0181022 A1, and US 2008/0038386 A1.

These may be used alone or by optionally blending two or more of them. It is preferable that, among the warming substances, at least one warming substance selected from the group consisting of the compounds (ε) and the natural products (ζ) is contained.

In a case where a cooling effect is aimed, the blending ratio of the warming substance to the cooling substance may be any value as long as the warming effect is not imparted by blending the warming substance, and in general, the blending amount of the warming substance is 0.001 to 0.95 times, preferably 0.01 to 0.5 times the total mass of the cooling agent composition. In the sensory stimulant composition including the cooling agent composition containing the methyl menthol derivative of the present invention, further improvement of the cooling effect can be achieved and the cooling effect is increased by adding the warming substance to the cooling agent composition at the above ratio.

In a case where a warming effect is aimed, the blending ratio of the cooling agent composition to the warming substance may be any value as long as the cooling effect is not imparted by blending the cooling agent composition, and in general, the blending amount of the cooling agent composition is 0.001 to 0.95 times, preferably 0.01 to 0.5 times the total mass of the warming substance.

Various synthetic aromachemical, natural essential oil, synthetic essential oil, citrus oil, animal aromachemical and the like may be mentioned as the flavor or fragrance components that may be contained with the cooling agent composition or the sensory stimulant composition of the present invention, and a broad range of flavor or fragrance components described, for example, in "Shuchi Kanyo Gijutsu Shu (Koryo) Daiichibu (Known/Common Technical Book (Flavor or Fragrances) Part I)" (Jan. 29, 1999, published by the Japanese Patent Office) may be used.

As typical ones among them, α-pinene, limonene, cis-3-hexenol, phenylethyl alcohol, styrallyl acetate, eugenol, rose oxide, linalool, benzaldehyde, muscone, Musk T (product name, manufactured by Takasago International Corporation), Thesaron (product name, manufactured by Takasago International Corporation), and the like may be mentioned.

The content of the cooling agent composition or the sensory stimulant composition in the flavor or fragrance composition containing the cooling agent composition of the present invention and the above flavor or fragrance component, or the sensory stimulant composition of the present invention and the above flavor or fragrance component can be adjusted based on the kinds of the flavor or fragrance component or other components to be mixed together therewith, application purposes of the flavor or fragrance composition, and the like. For example, in the case of a fragrance composition for fragrances or cosmetics, the content of the cooling agent composition or the sensory stimulant composition is generally from 0.00001 mass % to 90 mass %, preferably from 0.001 mass % to 50 mass %, and particularly preferably from 0.01 mass % to 20 mass %, based on the total mass of the flavor or fragrance composition.

In addition, in the case of a flavor composition for drinks or foods, the content of the cooling agent composition or the sensory stimulant composition is generally from 0.00001 mass % to 90 mass %, preferably from 0.0001 mass % to 50 mass %, and particularly preferably from 0.001 mass % to 30 mass %, based on the total mass of the flavor or fragrance composition.

As occasion demands, the cooling agent composition-containing flavor or fragrance composition containing the cooling agent composition, or the sensory stimulant composition-containing flavor or fragrance composition containing the sensory stimulant composition may contain one or two or more kinds of other fragrance retainers generally used in flavor or fragrance compositions. As the other fragrance retainers in that case, examples thereof include ethylene glycol, propylene glycol, dipropylene glycol, glycerin, hexyl glycol, benzyl benzoate, triethyl citrate, diethyl phthalate, hercolyn, medium chain fatty acid triglyceride, medium chain fatty acid diglyceride, and the like, and one or two or more thereof may be contained.

The cooling agent composition or the sensory stimulant composition of the present invention can be used for imparting the cool-feeling or the sensory stimulation to various products as described above, by the cooling agent composition or the sensory stimulant composition alone or by forming into the cooling agent composition-containing flavor or fragrance composition containing the cooling agent composition, or the sensory stimulant composition-containing flavor or fragrance composition containing the sensory stimulant composition.

The product, to which the cool-feeling or the sensory stimulation may be imparted by the cooling agent composition or sensory stimulant composition of the present invention itself or by the cooling agent composition-containing flavor or fragrance composition or the sensory stimulant composition-containing flavor or fragrance composition, is not particularly limited. Examples thereof include: drinks; foods; toiletry products such as cleaning agents, detergents for kitchen, and bleaching agents; air care products such as deodorants and aromatics; oral compositions; fragrances or cosmetics such as fragrance products, foundation cosmetics, finishing cosmetics, hair cosmetics, suntan cosmetics, and medicated cosmetics; hair care products; skin care products such as soaps; body care products such as body washers; bathing agents; cleaning agents for clothes; soft finishing agents for clothes; aerosol agents; daily necessities and household goods; tobacco; and quasi-drugs or pharmaceuticals.

As the drinks, examples thereof include drinks such as fruit juice drinks, fruit wines, milk drinks, carbonated drinks, soft drinks, health drinks, and alcohol-based drinks (such as beer, beer-flavored drinks, highball, and chuhai); tea drinks or luxury drinks such as green tea. Oolong tea, black tea, persimmon leaf tea, chamomile tea, low striped bamboo tea, mulberry tea, dokudami tea, Pu-er tea, mate tea, Rooibos tea, Gymnema tea, Guava tea, coffee, and cocoa; soups such as Japanese style soup, Western style soup and Chinese soup; various snack food and the like;

as the foods, examples thereof include ices such as ice creams, sherbets and ice candies; desserts such as jelly and pudding; western style confections such as cakes, cookies, chocolates and chewing gum, Japanese style confections such as bean-jam bun, sweet bean jelly and uiro; jams; candies; breads; flavor seasoning; various instant food; various snack food and the like;

as the oral compositions, examples thereof include dentifrice, oral cavity cleaner, mouth wash, troche, chewing gum, and the like;

as the fragrance products, examples thereof include perfume, eau de parfun, eau de toilette, eau de cologne, and the like;

as the foundation cosmetics, examples thereof include facial wash creams, vanishing creams, cleansing creams, cold creams, massage creams, milky lotions, skin lotions, beauty lotions, facial packs, makeup removers, and the like;

as the finishing cosmetics, examples thereof include foundations, face powders, solid face powders, talcum powders, rouges, lip balms, cheek rouges, eye liners, mascara, eye shadows, eyebrow pencils, eye packs, nail enamels, enamel removers, and the like; as the hair cosmetics, examples thereof include pomade, brilliantine, hair set lotions, hair sticks, hair solids, hair oils, hair treatments, hair creams, hair tonics, hair liquids, hair sprays, bandolines, revitalizing hair tonics, hair dyes, and the like;

as the suntan cosmetics, examples thereof include suntan products, sun-screen products, and the like;

as the medicated cosmetics, examples thereof include antiperspirants, after-shaving lotions or gels, permanent wave agents, medicated soaps, medicated shampoos, medicated skin cosmetics, and the like;

as the hair care products, examples thereof include shampoos, rinses, rinse-in-shampoos, conditioners, treatments, hair packs and the like;

as the soap, examples thereof include toilet soaps, bath soaps, perfume soaps, transparent soaps, synthetic soaps, and the like;

as the body washers, examples thereof include body soaps, body shampoos, hand soaps, face creams, and the like;

as the bath agents, examples thereof include bathing agents (such as bath salts, bath tablets, and bath liquids), foam bath (such as bubble bath), bath oils (such as bath perfumes, and bath capsules), milk-baths, bath jelly, bath cubes, and the like; as the detergents, examples thereof include heavy detergents for clothing use, light detergents for clothing use, liquid detergents, washing soaps, compact detergents, powder soaps, and the like;

as the soft finishing agents, examples thereof include softener, furniture care, and the like:

as the cleaners, examples thereof include cleansers, house cleaners, toilet cleaners, bath cleaners, glass cleaners, mildew removers, cleaners for drainpipe use, and the like;

as the kitchen cleaners, examples thereof include kitchen soaps, kitchen synthetic soaps, tableware cleaners, and the like;

as the bleaching agents, examples thereof include oxidation type bleaching agents (such as chlorine type bleaching agents, and oxygen type bleaching agents), reduction type bleaching agents (such as sulfur type bleaching agents), optical bleaching agents, and the like;

as the aerosol agents, examples thereof include spray type ones, powder sprays, and the like;

as the deodorants or aromatics, examples thereof include solid type ones, gel type ones, liquid type ones (aqueous and oily), and the like;

as the daily necessities and household goods, examples thereof include tissue papers, toilet papers, and the like;

as the tobacco, examples thereof include cigarettes, cigars, pipe tobacco, kiseru tobacco, hookah, smokeless tobacco, heat-type tobacco, electronic cigarettes, and the like;

as the quasi-drugs, examples thereof include liquid bath additives, mouthwashes, and repellents such as mist spray type ones and aqueous liquid type ones;

as the pharmaceuticals, examples thereof include medicinal cosmetics and medicinal lotions.

The dosage form of the methyl menthol derivative of the present invention may be in the form of a mixture. As another dosage form, there can be mentioned various dosage forms such as a liquid form obtained by dissolving the methyl menthol derivative in alcohols, polyhydric alcohols such as propylene glycol, glycerin, and dipropylene glycol, or esters such as triethyl citrate, benzyl benzoate, and diethyl phthalate;

natural gum such as gum Arabic, and tragant gum;

an emulsified form obtained by emulsifying the methyl menthol derivative with an emulsifier such as a glycerin fatty acid ester or a sucrose fatty acid ester;

a powder form obtained by coating the methyl menthol derivative with a film by using an excipient such as natural gum like gum Arabic, gelatin, and dextrin;

a solubilized form or a dispersed form obtained by solubilizing or dispersing the methyl menthol derivative by using a surfactant such as a nonionic surfactant, an anionic surfactant, a cationic surfactant, and an amphoteric surfactant; and a microcapsule obtained by treating the methyl menthol derivative with an encapsulating agent, and an arbitrary form may be selected and used depending on the purpose.

As a method of imparting the cool-feeling or the sensory stimulation to various products as described above by using the cooling agent composition or the sensory stimulant composition of the present invention, or the cooling agent composition-containing flavor or fragrance composition containing the same, or the sensory stimulant composition-containing flavor or fragrance composition containing the same, examples thereof are as follows:

depending on the kinds of the product to which the cool-feeling or the sensory stimulation is imparted or the final form of the product (for example, the form of the product such as a liquid form, a solid form, a powder form, a gel form, a mist form, and an aerosol form), the cooling agent composition or the sensory stimulant composition, or the cooling agent composition-containing flavor or fragrance composition containing the same, or the sensory stimulant composition-containing flavor or fragrance composition containing the same may be added or applied directly to the product;

the cooling agent composition or the sensory stimulant composition, or the cooling agent composition-containing flavor or fragrance composition containing the same, or the sensory stimulant composition-containing flavor or fragrance composition containing the same may be dissolved in, for example, an alcohol or a polyhydric alcohol such as propylene glycol or glycerin to form a liquid form, and then, it may be added or applied to the product;

the above composition may be formed into a solubilized form or a dispersed form by being solubilized or emulsification-dispersed by using natural gum such as gum Arabic or tragant gum or a surfactant (such as a nonionic surfactant like a glycerin fatty acid ester and a sucrose fatty acid ester, an anionic surfactant, a cationic surfactant, and an amphoteric surfactant), and then, they may be added or applied to the product;

the above compositions may be formed into a powder form obtained by coating with a film by using an excipient such as natural gum like gum Arabic, gelatin, or dextrin, and then, it may be added or applied to the product; and the above compositions may be formed into a microcapsule by a treatment with an encapsulating agent, and then, it may be added or applied to the product.

Further, the cooling agent composition or the sensory stimulant composition, or the cooling agent composition-containing flavor or fragrance composition containing the same, or the sensory stimulant composition-containing flavor or fragrance composition containing the same may be included in an inclusion agent such as cyclodextrin so as to stabilize the composition and also make it sustained-releasable, and then may be used.

The amount of adding or applying the cooling agent composition or the sensory stimulant composition to the product for imparting the cool-feeling or the sensory stimulation, can be adjusted depending on the kind or the form of the product, effects or actions of imparting the cool-feeling or the sensory stimulation required for the product, or the like. The addition amount or application amount of the cooling agent composition or the sensory stimulant composition is generally from 0.00001 mass % to 50 mass %, preferably from 0.0001 mass % to 20 mass %, and particularly preferably from 0.001 mass % to 5 mass %, based on the mass of the product.

In addition, the amount of adding or applying the flavor or fragrance composition to the product for imparting the cool-feeling or the sensory stimulation, can also be appropriately adjusted. The addition amount or application amount of the flavor or fragrance composition is generally from 0.00001 mass % to 50 mass %, preferably from 0.0001 mass % to 20 mass %, and particularly preferably from 0.001 mass % to 5 mass %, based on the mass of the product.

EXAMPLES

Hereinafter, the measurement of products in synthesis examples and examples was performed by using the following apparatuses and devices.

Nuclear Magnetic Resonance Spectrum: 1H-NMR: AM-500 (500 MHz) (manufactured by Bruker Co., Ltd.)

Internal Standard Substance: tetramethylsilane

Gas Chromatograph (GC): GC-2010AF (manufactured by Shimadzu Corporation)

Column: DB-WAX (30 m×0.32 mm×0.5 μm) (manufactured by Hewlett-Packard Company), IC-1 (30 m×0.25 mm×0.25 μm), (manufactured by Hewlett-Packard Company), Rtx-1 (30 m×0.25 mm×0.25 μm) (manufactured by Restek, Inc.) Chiral column (optical purity measurement): Beta DEX™ 225 (30 m×0.25 mm×0.25 μm), Beta DEX™ 325 (30 m×0.25 mm×0.25 μm) (manufactured by Supelco, Inc.)

High-Resolution Mass Spectrum (HRMS): JMS-T100GCV (manufactured by JEOL Ltd.), LCMS-IT-TOF (manufactured by Shimadzu Corporation)

Optical Rotation: JASCO P-1020 (manufactured by JASCO Corporation)

Melting Point: melting point measurement device (Serial No. 2678) (manufactured by Anatec Corporation)

The exemplary compounds (1-1) to (1-13) prepared in the following examples mainly include a mixture of trans-forms showing the structures of the above formulas (1-b) and (1-d).

In addition, in the exemplary compounds and comparative compounds shown below, Me represents a methyl group, and Ac represents an acetyl group.

[Example 1] Synthesis of Exemplary Compound (1-1) (N-(2-hydroxy-2-phenylethyl)-2-isopropyl-5,5-dimethyl cyclohexane carboxamide)

[Chem. 15]

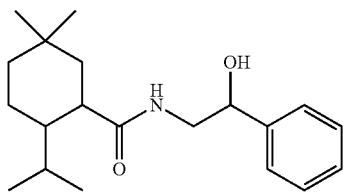

(1-1)

This reaction was performed under a nitrogen atmosphere. 5-methyl menthyl carboxylic acid (25 g, 126 mmol) which was obtained according to the method of WO2016/153011 A1, thionyl chloride (10.2 mL, 1.12 eq.), toluene (50 mL), and a few drops of dimethyl formamide (DMF) were added to a 100 mL four neck flask, and they were stirred for three hours at room temperature. Then, temperature of the inside of the system was cooled to 10° C. or lower, and a mixed solution of (±)-2-amino-1-phenylethanol (19.0 g, 1.1 eq.), toluene (75 mL), and triethylamine (22.8 mL) was slowly added thereto. After the mixture reacted for two and a half hours, the reaction solution was transferred to a separatory funnel, and tap water and ethyl acetate were added thereto to perform washing. The oil layer was washed twice with dilute hydrochloric acid, then once with a saturated saline solution, and dried by anhydrous magnesium sulfate. The obtained solution was concentrated under reduced pressure, and recrystallized with heptane/ethyl acetate, thereby obtaining N-(2-hydroxy-2-phenylethyl)-2-isopropyl-5,5-dimethyl cyclohexane carboxamide as a white crystal (29.2 g, yield 73%).

Melting Point: 105° C. to 110° C.
HRMS: Mass 318.2428 ([M+H]$^+$) Actual Measurement Value 318.2436
$^1$H-NMR (500 MHz, CDCl$_3$): δ 0.75 (dd, 3H. J=10.8, 7.0 Hz), 0.84-0.92 (m, 9H), 1.10-1.28 (m, 3H), 1.37-1.52 (m, 4H), 1.60-1.72 (m, 1H), 2.08-2.17 (m, 1H), 3.29-3.46 (m, 1H), 3.53-3.84 (m, 2H), 4.87-4.91 (m, 1H), 5.79 (br, 1H), 7.26-7.37 (m, 5H) (diastereomeric mixture)

[Example 2] Synthesis of Exemplary Compound (1-2) (N—((S)-2-hydroxy-2-phenylethyl)-2-isopropyl-5,5-dimethyl cyclohexane carboxamide)

[Chem. 16]

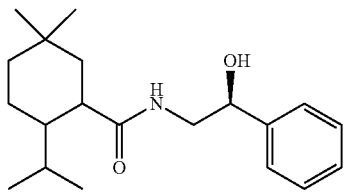

(1-2)

This reaction was performed under a nitrogen atmosphere. 5-methyl menthyl carboxylic acid (1.31 g, 6.63 mmol) which was obtained according to the method of WO2016/153011 A1, thionyl chloride (0.58 mL, 1.2 eq.), toluene (10 mL), and a few drops of DMF were added to a 100 mL four neck flask, and were stirred for three hours at room temperature. Then, temperature of the inside of the system was cooled to 10° C. or lower, and (S)-2-amino-1-phenylethanol (1.00 g, 1.1 eq.) and triethylamine (1.2 mL) were slowly added thereto. After the mixture reacted for two and a half hours, the reaction solution was transferred to a separatory funnel, and tap water and ethyl acetate were added thereto to perform washing. The oil layer was washed twice with dilute hydrochloric acid, then once with a saturated saline solution, and dried by anhydrous magnesium sulfate. The obtained solution was concentrated under reduced pressure, and refined by performing column chromatography (heptane/ethyl acetate), thereby obtaining N—((S)-2-hydroxy-2-phenylethyl)-2-isopropyl-5,5-dimethyl cyclohexane carboxamide as a white crystal (0.71 g, yield 34%).

Melting Point: 90° C. to 94° C.
HRMS: Mass 318.2428 ([M+H]$^+$) Actual Measurement Value 318.2430
$^1$H-NMR (500 MHz, CDCl$_3$): δ 0.75 (dd, 3H, J=10.8, 6.9 Hz), 0.85-0.92 (m, 9H), 1.10-1.28 (m, 3H), 1.37-1.52 (m, 4H), 1.60-1.72 (m, 1H), 2.08-2.17 (m, 1H), 3.29-3.45 (m, 1H), 3.54 (d, 1H, J=3.9 Hz (diastereomer)), 3.68 (d, 1H, J=3.3 Hz (diastereomer)), 3.65-3.84 (m, 1H), 4.87-4.91 (m, 1H), 5.79 (br, 1H), 7.26-7.37 (m, 5H) (diastereomer mixture).

[Example 3] Synthesis of Exemplary Compound (1-3) (N—((R)-2-hydroxy-2-phenylethyl)-2-isopropyl-5,5-dimethyl cyclohexane carboxamide)

[Chem. 17]

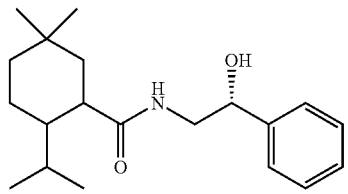

(1-3)

This reaction was performed under a nitrogen atmosphere. 5-methyl menthyl carboxylic acid (1.31 g, 6.63 mmol) which was obtained according to the method of WO2016/153011 A1, thionyl chloride (0.58 mL, 1.2 eq.), toluene (10 mL), and a few drops of DMF were added to a 100 mL four neck flask, and were stirred for three hours at room temperature. Then, temperature of the inside of the system was cooled to 10° C. or lower, and (R)-2-amino-1-phenylethanol (1.00 g, 1.1 eq.) and triethylamine (1.2 mL) were slowly added thereto. After the mixture reacted for two and a half hours, the reaction solution was transferred to a separatory funnel, and tap water and ethyl acetate were added thereto to perform washing. The oil layer was washed twice with dilute hydrochloric acid, then once with a saturated saline solution, and dried by anhydrous magnesium sulfate. The obtained solution was concentrated under reduced pressure, and refined by performing column chromatography (heptaneiethyl acetate), thereby obtaining (N—((R)-2-hydroxy-2-phenylethyl)-2-isopropyl-5,5-dimethyl cyclohexane carboxamide) as a white crystal (0.49 g, yield 23%).

Melting Point: 89° C. to 94° C.

HRMS: Mass 318.2428 ([M+H]+) Actual Measurement Value 318.2433

$^1$H-NMR (500 MHz, CDCl$_3$): δ 0.75 (dd, 3H, J=10.8, 6.9 Hz), 0.85-0.94 (m, 9H), 1.10-1.28 (m, 3H), 1.37-1.52 (m, 4H), 1.60-1.72 (m, 1H), 2.08-2.17 (m, 1H), 3.29-3.45 (m, 1H), 3.54-3.84 (m, 2H), 4.87-4.91 (m, 1H), 5.79 (br, 1H), 7.25-7.37 (m, 5H) (diastereomeric mixture).

[Example 4] Synthesis of Exemplary Compound (1-4) (2-(2-isopropyl-5,5-dimethyl cyclohexane carboxamide)-1-phenylethyl acetate)

[Chem. 18]

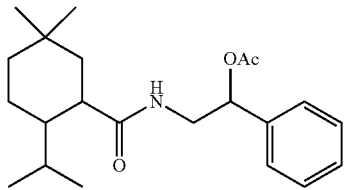

(1-4)

This reaction was performed under a nitrogen atmosphere. The exemplary compound (1-1) obtained in Example 1 (620 mg, 1.95 mmol), acetyl chloride (0.15 mL, 1.1 eq.), triethylamine (0.81 mL), and toluene (10 mL) were added to a 100 mL four neck flask, and were stirred for two hours at room temperature. Then, the reaction solution was transferred to a separatory funnel, and tap water and ethyl acetate were added thereto to perform washing. The oil layer was washed twice with dilute hydrochloric acid, then once with a saturated saline solution, and dried by anhydrous magnesium sulfate. The obtained solution was concentrated under reduced pressure, and refined by performing column chromatography (heptane/ethyl acetate), thereby obtaining (2-(2-isopropyl-5,5-dimethyl cyclohexane carboxamide)-1-phenylethyl acetate) as an amorphous solid (275 mg, yield 39%).

HRMS: Mass 359.2460 Actual Measurement Value 359.2431

$^1$H-NMR (500 MHz, CDCl$_3$): δ 0.76 (dd, 3H, J=13.8, 6.9 Hz), 0.83-0.94 (m, 9H), 1.10-1.28 (m, 2H), 1.33-1.51 (m, 4H), 1.55-1.69 (m, 2H), 2.03-2.09 (m, 1H), 2.10 (d, 3H, J=4.8 Hz), 3.41-3.88 (m, 2H), 5.54 (br, 1H), 5.86 (m, 1H), 7.29-7.38 (m, 5H) (diastereomeric mixture).

[Example 5] Synthesis of Exemplary Compound (1-5) (2-isopropyl-5,5-dimethyl-N-(2-oxo-2-phenylethyl) cyclohexane carboxamide)

[Chem. 19]

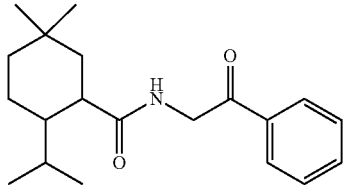

(1-5)

This reaction was performed under a nitrogen atmosphere. 5-methyl menthyl carboxylic acid (963 mg, 4.86 mmol) which was obtained according to the method of WO2016/153011 A1, thionyl chloride (0.42 mL, 1.2 eq.), toluene (10 mL), and a few drops of DMF were added to a 100 mL four neck flask, and were stirred for three hours at room temperature. Then, temperature of the inside of the system was cooled to 10° C. or lower, and 2-aminoacetophenone hydrochloride (1.00 g, 1.2 eq.) and triethylamine (1.5 mL) were slowly added thereto. After the mixture was heated and stirred at 40° C. and was made to react for two and a half hours, the reaction solution was transferred to a separatory funnel, and tap water and ethyl acetate were added thereto to perform washing. The oil layer was washed twice with dilute hydrochloric acid, then once with a saturated saline solution, and dried by anhydrous magnesium sulfate. The obtained solution was concentrated under reduced pressure, and refined by performing column chromatography (heptane/ethyl acetate), thereby obtaining 2-isopropyl-5,5-dimethyl-N-(2-oxo-2-phenylethyl) cyclohexane carboxamide as a white crystal (632 mg, yield 77%).

Melting Point: 85° C. to 88° C.

HRMS: Mass 315.2198 Actual Measurement Value 315.2190

$^1$H-NMR (500 MHz, CDCl$_3$): δ 0.84 (d, 3H, J=6.9 Hz), 0.89-0.94 (m, 9H), 1.17-1.30 (m, 2H), 1.41-1.60 (m, 5H), 1.67-1.73 (m, 1H), 2.33 (td, 1H, J=11.1, 5.0 Hz), 4.78 (d, 2H, J=4.3 Hz), 6.52 (br, 1H), 7.51 (t, 2H, J=7.8 Hz), 7.63 (t, 1H, J=7.5 Hz), 7.99 (d, 1H, J=7.5 Hz).

[Example 6] Synthesis of Exemplary Compound (1-6) (2-isopropyl-5,5-dimethyl-N-(2-phenylpropyl) cyclohexane carboxamide)

[Chem. 20]

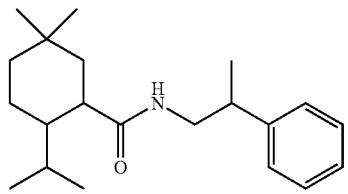

(1-6)

This reaction was performed under a nitrogen atmosphere. 5-methyl menthyl carboxylic acid (963 mg, 4.86 mmol) which was obtained according to the method of WO2016/153011 A1, thionyl chloride (0.42 mL, 1.2 eq.), toluene (10 mL), and a few drops of DMF were added to a 100 mL four neck flask, and were stirred for three hours at room temperature. Then, temperature of the inside of the system was cooled to 10° C. or lower, and (±)-1-methyl-1-phenylethylamine (722 mg, 1.1 eq.) and triethylamine (0.81 mL) were slowly added thereto. After the mixture was heated and stirred at 40° C. and was made to react for two and a half hours, the reaction solution was transferred to a separatory funnel, and tap water and ethyl acetate were added thereto to perform washing. The oil layer was washed twice with dilute hydrochloric acid, then once with a saturated saline solution, and dried by anhydrous magnesium sulfate. The obtained solution was concentrated under reduced pressure, and refined by performing column chromatography (heptane/ethyl acetate), thereby obtaining 2-isopropyl-5,5-dimethyl-N-(2-phenylpropyl) cyclohexane carboxamide as a white-to-pale-yellow solid (1.05 g, yield 68%).

Melting Point: 80° C. to 85° C.

HRMS: Mass 315.2562 Actual Measurement Value 315.2567

$^1$H-NMR (500 MHz, CDCl$_3$): δ 0.66 (dd, 3H, J=17.1, 6.9 Hz), 0.79-0.92 (m, 9H), 1.05-1.21 (m, 2H), 1.26 (d, 3H, J=7.0 Hz), 1.28-1.47 (m, 5H), 1.48-1.69 (m, 1H), 1.91-2.00 (m, 1H), 2.89-3.02 (m, 1H), 3.11-3.39 (m, 1H), 3.46-3.76 (m, 1H), 5.23 (br, 1H), 7.15-7.36 (m, 5H) (diastereomeric mixture).

[Example 7] Synthesis of Exemplary Compound (1-7) (2-isopropyl-5,5-dimethyl-N—((S)-2-phenylpropyl) cyclohexane carboxamide)

[Chem. 21]

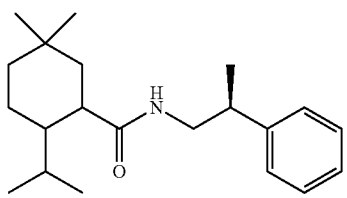 [SMILES: CC(C)C1CCC(C)(C)CC1C(=O)NC[C@@H](C)c1ccccc1]

(1-7)

This reaction was performed under a nitrogen atmosphere. 5-methyl menthyl carboxylic acid (1.00 g, 5.04 mmol) which was obtained according to the method of WO2016/153011 A1, thionyl chloride (0.40 mL, 1.1 eq.), toluene (10 mL), and a few drops of DMF were added to a 100 mL four neck flask, and were stirred for three hours at room temperature. Then, temperature of the inside of the system was cooled to 10° C. or lower, and (S)-1-methyl-1-phenylethylamine (0.79 mL, 1.1 eq.) and triethylamine (0.84 mL) were slowly added thereto. After the mixture was heated and stirred at 40° C. and was made to react for two and a half hours, the reaction solution was transferred to a separatory funnel, and tap water and ethyl acetate were added thereto to perform washing. The oil layer was washed twice with dilute hydrochloric acid, then once with a saturated saline solution, and dried by anhydrous magnesium sulfate. The obtained solution was concentrated under reduced pressure, and refined by performing column chromatography (heptane/ethyl acetate), thereby obtaining 2-isopropyl-5,5-dimethyl-N—((S)-2-phenylpropyl) cyclohexane carboxamide as a colorless amorphous solid (1.26 g, yield 80%).

Melting Point: 125° C. to 133° C.

HRMS: Mass 316.2635 ([M+H]$^+$) Actual Measurement Value 316.2635

$^1$H-NMR (500 MHz, CDCl$_3$): δ 0.67 (dd, 3H, J=17.1, 7.0 Hz), 0.79-0.92 (m, 9H), 1.05-1.21 (m, 2H), 1.26 (d, 3H, J=7.0 Hz), 1.28-1.47 (m, 5H), 1.48-1.69 (m, 1H), 1.91-2.01 (m, 1H), 2.89-3.02 (m, 1H), 3.11-3.39 (m, 1H), 3.46-3.76 (m, 1H), 5.22 (br, 1H), 7.17-7.36 (m, 5H) (diastereomeric mixture).

[Example 8] Synthesis of Exemplary Compound (1-8) (2-isopropyl-5,5-dimethyl-N—((R)-2-phenylpropyl) cyclohexane carboxamide)

[Chem. 22]

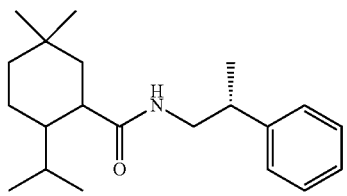 [SMILES: CC(C)C1CCC(C)(C)CC1C(=O)NC[C@H](C)c1ccccc1]

(1-8)

This reaction was performed under a nitrogen atmosphere. 5-methyl menthyl carboxylic acid (1.00 g, 5.04 mmol) which was obtained according to the method of WO2016/153011 A1, thionyl chloride (0.40 mL, 1.1 eq.), toluene (10 mL), and a few drops of DMF were added to a 100 mL four neck flask, and were stirred for three hours at room temperature. Then, temperature of the inside of the system was cooled to 10° C. or lower, and (R)-1-methyl-1-phenylethylamine (0.79 mL, 1.1 eq.) and triethylamine (0.84 mL) were slowly added thereto. After the mixture was heated and stirred at 40° C. and was made to react for two and a half hours, the reaction solution was transferred to a separatory funnel, and tap water and ethyl acetate were added thereto to perform washing. The oil layer was washed twice with dilute hydrochloric acid, then once with a saturated saline solution, and dried by anhydrous magnesium sulfate. The obtained solution was concentrated under reduced pressure, and refined by performing column chromatography (heptane/ethyl acetate), thereby obtaining 2-isopropyl-5,5-dimethyl-N—((R)-2-phenylpropyl) cyclohexane carboxamide as a white solid (1.21 g, yield 76%).

Melting Point: 127° C. to 134° C.

HRMS: Mass 316.2635 ([M+H]$^+$) Actual Measurement Value 316.2636

$^1$H-NMR (500 MHz, CDCl$_3$): δ 0.66 (dd, 3H, J=17.1, 7.0 Hz), 0.79-0.92 (m, 9H), 1.05-1.21 (m, 2H), 1.26 (d, 3H, J=7.0 Hz), 1.28-1.47 (m, 5H), 1.48-1.69 (m, 1H), 1.91-2.01 (m, 1H), 2.89-3.02 (m, 1H), 3.11-3.39 (m, 1H), 3.46-3.76 (m, 1H), 5.22 (br, 1H), 7.15-7.36 (m, 5H) (diastereomeric mixture).

[Example 9] Synthesis of Exemplary Compound (1-9) (N-(4-hydroxyphenylethyl)-2-isopropyl-5,5-dimethyl cyclohexane carboxamide)

[Chem. 23]

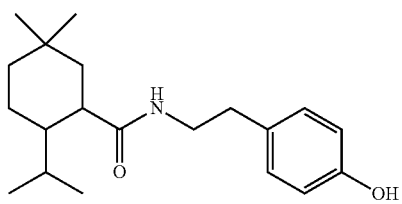 [SMILES: CC(C)C1CCC(C)(C)CC1C(=O)NCCc1ccc(O)cc1]

(1-9)

This reaction was performed under a nitrogen atmosphere. 5-methyl menthyl carboxylic acid (1.00 g, 5.04 mmol) which was obtained according to the method of WO2016/153011 A1, thionyl chloride (0.40 mL, 1.1 eq.), toluene (10 mL), and a few drops of DMF were added to a 100 mL four neck flask, and were stirred for three hours at room temperature. Then, temperature of the inside of the system was cooled to 10° C. or lower, and tyramine (0.83 g, 1.2 eq.) and triethylamine (1.4 mL) were slowly added thereto. After the mixture was heated and stirred at 70° C. and made to react for four and a half hours, the reaction solution was transferred to a separatory funnel, and tap water, chloroform, and THF were added thereto to perform washing. The oil layer was washed twice with dilute hydrochloric acid, then once with a saturated saline solution, and dried by anhydrous magnesium sulfate. The obtained solution was concentrated under reduced pressure, and refined by performing column chromatography (heptane/ethyl acetate), thereby obtaining N-(4-hydroxyphenylethyl)-2-isopropyl-5,5-dimethyl cyclohexane carboxamide as a pale-yellow solid (0.76 g, yield 47%).

Melting Point: 183° C. to 190° C.

HRMS: Mass 318.2428 ([M+H]$^+$) Actual Measurement Value 318.2415

$^1$H-NMR (500 MHz, DMSO-D$_6$): δ 0.72 (d, 3H, J=6.9 Hz), 0.80 (d, 3H, J=6.9 Hz), 0.84-0.89 (m, 6H), 1.03-1.13 (m, 2H), 1.20-1.41 (m, 6H), 1.49 (quid, 1H, J=7.1, 2.2 Hz), 2.14-2.23 (m, 1H), 2.56 (t, 2H, J=7.2 Hz), 3.06-3.14 (m, 1H), 3.21-3.30 (m, 1H), 6.63-6.67 (m, 2H), 6.96 (d, 2H, J=8.4 Hz), 7.81 (t, 1H, J=5.6 Hz).

[Example 10] Synthesis of Exemplary Compound (1-10) (2-isopropyl-N-(4-methoxyphenylethyl)-5,5-dimethyl cyclohexane carboxamide)

[Chem. 24]

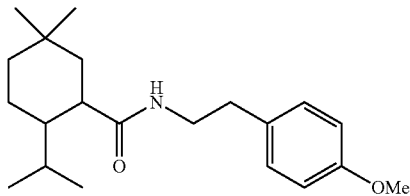 [SMILES: COc1ccc(CCNC(=O)C2CC(C)(C)CCC2C(C)C)cc1]

(1-10)

This reaction was performed under a nitrogen atmosphere. 5-methyl menthyl carboxylic acid (1.00 g, 5.04 mmol) which was obtained according to the method of WO2016/153011 A1, thionyl chloride (0.40 mL, 1.1 eq.), toluene (10 mL), and a few drops of DMF were added to a 100 mL four neck flask, and were stirred for three hours at room temperature. Then, temperature of the inside of the system was cooled to 10° C. or lower, and 2-(4-methoxyphenyl) ethylamine (0.89 mL, 1.2 eq.) and triethylamine (1.4 mL) were slowly added thereto. After the mixture was heated and stirred at 40° C. and was made to react for two and a half hours, the reaction solution was transferred to a separatory funnel, and tap water and ethyl acetate were added thereto to perform washing. The oil layer was washed twice with dilute hydrochloric acid, then once with a saturated saline solution, and dried by anhydrous magnesium sulfate. The obtained solution was concentrated under reduced pressure, and refined by performing column chromatography (heptane/ethyl acetate), thereby obtaining 2-isopropyl-N-(4-methoxyphenylethyl)-5,5-dimethyl cyclohexane carboxamide as a white solid (1.29 g, yield 77%).

Melting Point: 86° C. to 88° C.

HRMS: Mass 332.2584 ([M+H]$^+$) Actual Measurement Value 332.2572

$^1$H-NMR (500 MHz, CDCl$_3$): δ 0.73 (d, 3H, J=6.9 Hz), 0.83-0.90 (m, 9H), 1.04-1.24 (m, 2H), 1.35-1.49 (m, 5H), 1.64 (quid, 1H, J=6.8, 2.5 Hz), 2.02 (td, 1H, J=11.4, 4.2 Hz), 2.75 (td, 2H, J=6.8, 1.8 Hz), 3.37-3.45 (m, 1H), 3.53-3.61 (m, 1H), 3.79 (s, 3H), 5.35 (br, 1H), 6.85 (d, 2H, J=8.7 Hz), 7.01 (d, 1H, J=8.7 Hz).

[Example 11] Synthesis of Exemplary Compound (1-11) (N-(3,4-dihydroxyphenylethyl)-2-isopropyl-5,5-dimethyl cyclohexane carboxamide)

[Chem. 25]

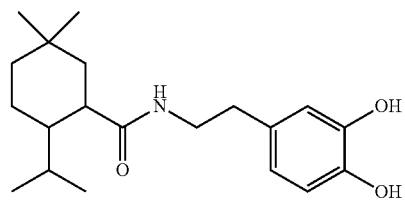 [SMILES: CC(C)C1CCC(C)(C)CC1C(=O)NCCc1ccc(O)c(O)c1]

(1-11)

This reaction was performed under a nitrogen atmosphere. 5-methyl menthyl carboxylic acid (1.00 g, 5.04 mmol) which was obtained according to the method of WO2016/153011 A1, thionyl chloride (0.40 mL, 1.1 eq.), toluene (10 mL), and a few drops of DMF were added to a 100 mL four neck flask, and were stirred for three hours at room temperature. Then, temperature of the inside of the system was cooled to 10° C. or lower, and dopamine hydrochloride (1.05 g, 1.1 eq.) and triethylamine (2.1 mL) were slowly added thereto. After the mixture was heated and stirred at 60° C. for four and a half hours, the reaction solution was transferred to a separatory funnel, and tap water, chloroform, and THF were added thereto to perform washing. The oil layer was washed twice with dilute hydrochloric acid, then once with a saturated saline solution, and dried by anhydrous magnesium sulfate. The obtained solution was concentrated under reduced pressure, and refined by performing column chromatography (heptane/ethyl acetate), thereby obtaining N-(3,4-dihydroxyphenylethyl)-2-isopropyl-5,5-dimethyl cyclohexane carboxamide as a light-orange amorphous solid (0.20 g, yield 12%).

HRMS: Mass 334.2377 ([M+H]$^+$) Actual measurement value 334.2387

$^1$H-NMR (500 MHz, DMSO-D$_6$): δ 0.73 (d, 3H, J=6.9 Hz), 0.80 (d, 3H, J=6.9 Hz), 0.83-0.88 (m, 6H), 1.06-1.14 (m, 2H), 1.23-1.39 (m, 5H), 1.47-1.54 (m, 1H), 2.14-2.21 (m, 1H), 2.46-2.54 (m, 2H), 3.08-3.14 (m, 1H), 3.18-3.26 (m, 1H), 6.41 (dd, 1H, J=8.0, 2.0 Hz), 6.55 (d, 1H, J=2.0 Hz), 6.61 (d, 1H, J=7.9 Hz), 7.81 (t, 1H, J=5.5 Hz), 8.52-8.70 (br, 2H).

[Example 12] Synthesis of Exemplary Compound (1-12) (N-(3,4-dimethoxyphenylethyl)-2-isopropyl-5,5-dimethyl cyclohexane carboxamide)

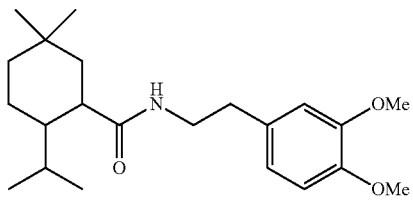 [SMILES: COc1ccc(CCNC(=O)C2CC(C)(C)CCC2C(C)C)cc1OC]

(1-12)

This reaction was performed under a nitrogen atmosphere. 5-methyl menthyl carboxylic acid (1.00 g, 5.04 mmol) which was obtained according to the method of WO2016/153011 A1, thionyl chloride (0.40 mL, 1.1 eq.), toluene (15 mL), and a few drops of DMF were added to a 100 mL four neck flask, and were stirred for three hours at room temperature. Then, temperature of the inside of the system was cooled to 10° C. or lower, and homoveratrylamine (1.16 g, 1.1 eq.) and triethylamine (0.91 mL) were slowly added thereto. After the mixture was stirred for two hours at room temperature, the reaction solution was transferred to a separatory funnel, and tap water and ethyl acetate were added thereto to perform washing. The oil layer was washed twice with dilute hydrochloric acid, then once with a saturated saline solution, and dried by anhydrous magnesium sulfate. The obtained solution was concentrated under reduced pressure, and refined by performing column chromatography (heptane/ethyl acetate), thereby obtaining N-(3,4-dimethoxyphenylethyl)-2-isopropyl-5,5-dimethyl cyclohexane carboxamide as a white solid (1.49 g, yield 82%).

Melting Point: 85° C. to 89° C.
HRMS: Mass 361.2617 Actual Measurement Value 361.2633
$^1$H-NMR (500 MHz, CDCl$_3$): δ 0.73 (d, 3H, J=6.9 Hz), 0.83-0.90 (m, 9H), 1.07-1.25 (m, 2H), 1.35-1.50 (m, 5H), 1.60-1.68 (m, 1H), 2.02 (td, 1H, J=11.3, 4.3 Hz), 2.70-2.81 (m, 2H), 3.41-3.48 (m, 1H), 3.58 (hex, 1H, J=6.8 Hz), 3.87 (d, 6H, J=3.1 Hz), 5.38 (br, 1H), 6.70-6.75 (m, 2H), 6.78-6.84 (m, 1H).

[Example 13] Synthesis of Exemplary Compound (1-13) (2-isopropyl-5,5-dimethyl-N-phenylethyl cyclohexane carboxamide)

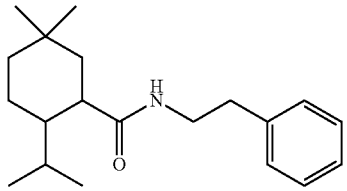 [SMILES: CC(C)C1CCC(C)(C)CC1C(=O)NCCc1ccccc1]

(1-13)

This reaction was performed under a nitrogen atmosphere. 5-methyl menthyl carboxylic acid (1.00 g, 5.04 mmol) which was obtained according to the method of WO2016/153011 A1, thionyl chloride (0.40 mL, 1.1 eq.), toluene (25 mL), and a few drops of DMF were added to a 100 mL four neck flask, and were stirred for three hours at room temperature. Then, temperature of the inside of the system was cooled to 10° C. or lower, and phenethylamine (0.70 mL, 1.1 eq.) and triethylamine (0.91 mL) were slowly added thereto. After the mixture was stirred for two hours at room temperature, the reaction solution was transferred to a separatory funnel, and tap water and ethyl acetate were added thereto to perform washing. The oil layer was washed twice with dilute hydrochloric acid, then once with a saturated saline solution, and dried by anhydrous magnesium sulfate. The obtained solution was concentrated under reduced pressure, and refined by performing column chromatography (heptane/ethyl acetate), thereby obtaining 2-isopropyl-5,5-dimethyl-N-phenylethyl cyclohexane carboxamide as a white solid (1.12 g, yield 73%).

Melting Point: 90° C. to 93° C.
HRMS: Mass 302.2478 ([M+H]$^+$) Actual Measurement Value 302.2478
$^1$H-NMR (500 MHz, CDCl$_3$): 50.73 (d, 3H, J=6.9 Hz), 0.83-0.92 (m, 9H), 1.06-1.24 (m, 2H), 1.34-1.48 (m, 5H), 1.65 (quid, 1H, J=6.9, 2.5 Hz), 2.02 (td, 1H, J=11.3, 4.4 Hz), 2.75-2.85 (m, 2H), 3.41-3.49 (m, 1H), 3.61 (hex, 1H, J=6.8 Hz), 5.37 (br, 1H), 7.16-7.34 (m, 5H).

[Example 14] Sensory Evaluation of Exemplary Compound (1-1)

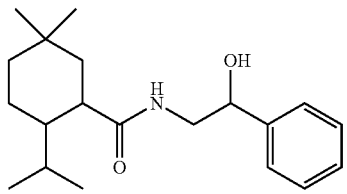

(1-1)

(Comparative Compound 1)

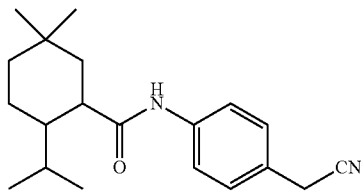

(Comparative Compound 2)

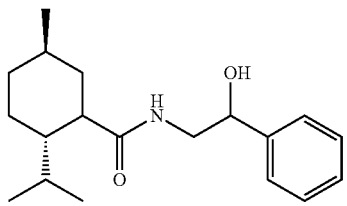

(Comparative Compound 3)

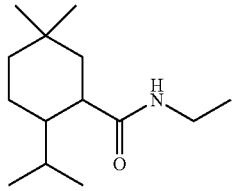

(Comparative Compound 4)

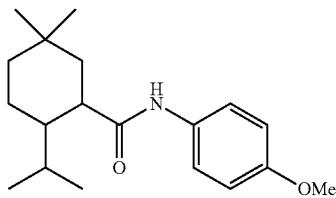

The sensory evaluation was performed by comparing the exemplary compound (1-1) with the so far known comparative compounds 1 to 4. Comparative compounds 1, 3, and 4 were synthesized according to the method described in WO 2016/153011 A1, and comparative compound 2 was synthesized according to the method described in WO 2005/020897 A1. The exemplary compound (1-1) and comparative compounds 1 to 4 were separately prepared into a 30 ppm aqueous solution, and the aqueous solution was used to perform the evaluation.

The evaluation was performed by three flavorists. The aqueous solution was taken into the mouth and spat out after the mouth was rinsed, and intensity, persistence, and quality of a cool-feeling in the oral cavity were evaluated.

[Sensory Findings]

The exemplary compound (1-1) had a very strong cool-feeling, and the cool-feeling was clearly stronger than those of the comparative compounds 3 and 4. In addition, the cool-feeling lasted for 60 minutes or longer.

Comparative compound 2 had the same cooling intensity and persistence as those of the exemplary compound (1-1), and the cool-feeling thereof was very strong and persistent.

Regarding the start of the cool-feeling, the exemplary compound (1-1) was clearly faster than the comparative compounds 1 to 4. A strong cool-feeling was felt when the exemplary compound (1-1) was put in mouth, and the miscellaneous tastes of the exemplary compound (1-1) such as bitterness were less than those of the comparative compounds 2 to 4.

Regarding the quality of the cool-feeling, the cool-feeling produced by the exemplary compound (1-1) was sharper and richer than those produced by the comparative compounds 1 to 4. In addition, the exemplary compound (1-1) had burning and tingling feelings weaker than those of the comparative compounds 1 to 4, and had a clear cool-feeling.

[Example 15] Sensory Evaluation of Exemplary Compound (1-2)

[Chem. 29]

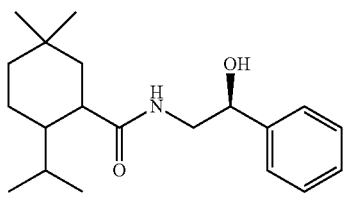

(1-2)

A 30 ppm aqueous solution of the exemplary compound (1-2) was prepared and used to perform the evaluation.

The evaluation was performed by three flavorists. The aqueous solution was taken into the mouth and spat out after the mouth was rinsed, and intensity, persistence, and quality of a cool-feeling in the oral cavity were evaluated.

[Sensory Findings]

The cool-feeling of the exemplary compound (1-2) was very strong, and lasted for 90 minutes or longer.

A strong cool-feeling was felt when the exemplary compound (1-2) was put in the mouth, and bitterness was not felt. As the quality of the cool-feeling, the cool-feeling was sharp and rich, and burning and tingling feelings were not felt.

[Example 15] Sensory Evaluation of Exemplary Compound (1-3)

[Chem. 30]

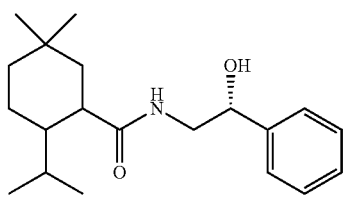

(1-3)

A 30 ppm aqueous solution of the exemplary compound (1-3) was prepared and used to perform the evaluation.

The evaluation was performed by three flavorists. The aqueous solution was taken into the mouth and spat out after the mouth was rinsed, and intensity, persistence, and quality of a cool-feeling in the oral cavity were evaluated.

[Sensory Findings]

The cool-feeling of the exemplary compound (1-3) was very strong, and lasted for 60 minutes or longer.

A strong cool-feeling was felt when the exemplary compound (1-3) was put in the mouth, and bitterness was not felt. As the quality of the cool-feeling, the cool-feeling was sharp and rich, and burning and tingling feelings were not felt.

[Example 17] Sensory Evaluation of Exemplary Compound (1-5)

[Chem. 31]

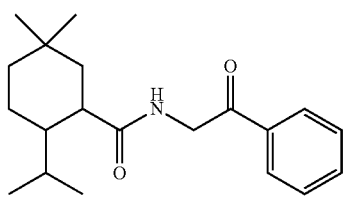

(1-5)

A 30 ppm aqueous solution of the exemplary compound (1-5) was prepared and used to perform the evaluation.

The evaluation was performed by three flavorists. The aqueous solution was taken into the mouth and spat out after the mouth was rinsed, and intensity, persistence, and quality of a cool-feeling in the oral cavity were evaluated.

[Sensory Findings]

As the exemplary compound (1-5), the cool-feeling was gradually felt strongly and very strongly at the peak time, and other feelings and the tingling feeling were hardly felt. The cool-feeling lasted for 60 minutes or longer.

[Example 18] Toothpaste Scenting Evaluation

[Chem. 32]

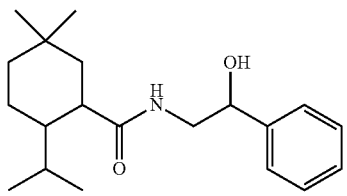

(1-1)

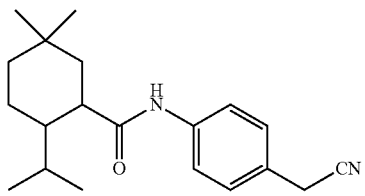

(Comparative Compound 1)

A sensory evaluation was performed on a toothpaste that was scented with 1-menthol and the comparative compound 1, or 1-menthol and the exemplary compound (1-1).

Toothpaste (A) to (C) was prepared according to the following formulations.

(A) toothpaste base 990 g+toothpaste flavor BASE 4 g+1-menthol 4 g+ethyl alcohol (EtOH) 2 g (B) toothpaste base 990 g+toothpaste flavor BASE 4 g+1-menthol 4 g+comparative compound 1 (1% in EtOH) 2 g (C) toothpaste base 990 g+toothpaste flavor BASE 4 g+1-menthol 4 g+exemplary compound (1-1) (1% in EtOH) 2 g The prescription for toothpaste flavor BASE is as follows.

TABLE 1

| (Component) | (Blending Amount g) |
|---|---|
| Anethole | 0.6 |
| Eucalyptol | 0.2 |
| Lemon oil | 0.1 |
| Mentha white oil | 1.0 |
| Peppermint oil | 1.5 |
| Propylene Glycol (PG) | 0.6 |
| Total Amount | 4.0 |

The prescription for toothpaste base is as follows.

TABLE 2

| (Component) | (Blending Amount g) |
|---|---|
| Calcium carbonate | 400.0 |
| Silicic anhydride | 16.5 |

TABLE 2-continued

| (Component) | (Blending Amount g) |
|---|---|
| Sorbitol solution (70%) | 240.0 |
| Sodium lauryl sulfate | 13.0 |
| Sodium carboxymethyl cellulose | 12.5 |
| Carrageenan | 3.0 |
| Sodium benzoate | 4.0 |
| Sodium saccharin | 1.5 |
| Purified water | 259.5 |
| Propylene Glycol (PG) | 40.0 |
| Total Amount | 990.0 |

The evaluation was performed by three flavorists. About 1 g of toothpaste was placed on a toothbrush, and the teeth were brushed for about five minutes in a usual brushing manner. The teeth were brushed and the mouth was rinsed, and then intensity, persistence, and quality of a cool-feeling in the oral cavity were evaluated.

[Evaluation Comment]

Toothpaste (B) and toothpaste (C) have cooling effects stronger than that of toothpaste (A), and the toothpaste (C) has the same cooling effect as the toothpaste (B). In addition, the toothpaste (C) clearly exhibits a flavor profile of the toothpaste flavor BASE, and the cool-feeling thereof is also clear, as compared with the toothpaste (B). Both the toothpaste (B) and the toothpaste (C) exhibited a cooling effect of 30 minutes or longer.

[Example 19] Mouthwash Scenting Evaluation

[Chem. 33]

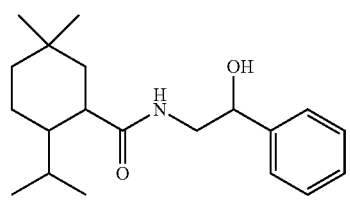

(1-1)

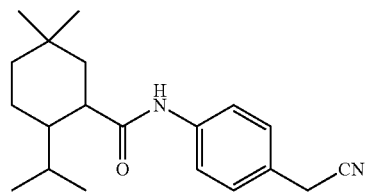

(Comparative Compound 1)

A sensory evaluation was performed on a mouthwash that was scented with 1-menthol and the comparative compound 1, or 1-menthol and the exemplary compound (1-1).

Mouthwashes (D) to (F) were prepared according to the following formulations.

(D) mouthwash base 999 g+mouthwash flavor BASE 0.35 g+1-menthol 0.45 g+ethyl alcohol (EtOH) 0.2 g (E) mouthwash base 999 g+mouthwash flavor BASE 0.35 g+1-menthol 0.45 g+comparative compound 1 (10% in EtOH) 0.2 g (F) mouthwash base 999 g+mouthwash flavor BASE 0.35 g+1-menthol 0.45 g+exemplary compound (1-1) (10% in EtOH) 0.2 g The prescription for the mouthwash flavor BASE is as follows.

TABLE 3

| (Component) | (Blending Amount g) |
|---|---|
| Anethole | 0.02 |
| 1-carvone | 0.01 |
| Mentha white oil | 0.05 |
| Peppermint oil | 0.20 |
| Propylene Glycol (PG) | 0.07 |
| Total Amount | 0.35 |

In addition, the prescription for the mouthwash base is as follows.

TABLE 4

| (Component) | (Blending Amount g) |
|---|---|
| Refined glycerin | 100.0 |
| Polyoxyethylene cured castor oil 60 | 10.0 |
| Sodium benzoate | 0.5 |
| Sodium saccharin | 0.1 |
| Purified water | 838.4 |
| Ethyl alcohol 95% | 50.0 |
| Total Amount | 999.0 |

The evaluation was performed by three flavorists. 20 mL of mouthwashes were taken into the mouth and spat out after the mouth was rinsed, and intensity, persistence, and quality of a cool-feeling in the oral cavity were evaluated.
[Evaluation Comment]
A mouthwash (E) and a mouthwash (F) had cooling effects stronger than that of a mouthwash (D), and the mouthwash (F) had the same cooling effect as the mouthwash (E). In addition, the mouthwash (F) clearly exhibited a mint flavor profile of the mouthwash flavor BASE, and the cool-feeling thereof was also clear, as compared with the mouthwash (E). Both the mouthwash (E) and the mouthwash (F) exhibited a cooling effect of 30 minutes or longer.

[Example 20] Chewing Gum Scenting Evaluation

[Chem. 34]

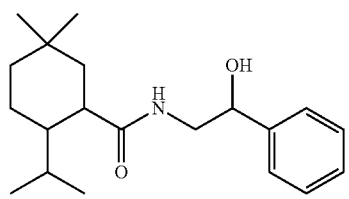

(1-1)

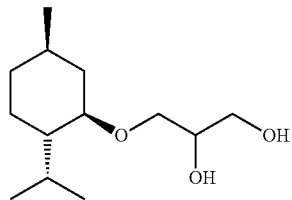

(Comparative Compound 5)

A sensory evaluation was performed on a chewing gum that was scented with 1-menthol and the so far known comparative compound 5 ("Coolact (registered trademark) 10" manufactured by Takasago International Corporation), or 1-menthol and the exemplary compound (1-1).

Chewing gum (G) to (I) was prepared according to the following formulations.
(G) chewing gum base 990 g+peppermint flavor BASE 7.3 g+1-menthol 0.7 g+ethyl alcohol (EtOH) 2 g
(H) chewing gum base 990 g+peppermint flavor BASE 7.3 g+1-menthol 0.7 g+comparative compound 5.2 g
(I) chewing gum base 990 g+peppermint flavor BASE 7.3 g+1-menthol 0.7 g+exemplary compound (1-1) (10% in EtOH) 2 g
The prescription for peppermint flavor BASE is as follows.

TABLE 5

| (Component) | (Blending Amount g) |
|---|---|
| Eucalyptol | 0.3 |
| Mentha white oil | 3.0 |
| Peppermint oil | 4.0 |
| Total Amount | 7.3 |

The prescription for the chewing gum BASE is as follows.

TABLE 6

| (Component) | (Blending Amount g) |
|---|---|
| Xylitol | 320.0 |
| Maltitol | 338.8 |
| Gum base | 280.0 |
| Reduced starch saccharide (BR1X70) | 40.0 |
| Glycerin | 10.0 |
| Acesulfame K | 0.6 |
| Aspartame | 0.6 |
| Total Amount | 990.0 |

The evaluation was performed by three flavorists. 1 g of chewing gum was taken into the mouth, chewed about five minutes and spat out, and then, intensity, persistence, and quality of a cool-feeling in the oral cavity were evaluated.
[Evaluation Comment]
A chewing gum (H) and a chewing gum (I) had a cooling effect stronger than a chewing gum (G), and the chewing gum (I) had a cooling effect equal to or stronger than that of the chewing gum (H) even though the blending amount of the cooling agent in the chewing gum (I) was 1/10 of that of the chewing gum (H). Further, chewing gum (I) exhibited a somewhat sharp cool-feeling from the beginning of chewing, and a well-ventilated cool-feeling spread in the oral cavity. In addition, a cooling effect of 30 minutes or longer was felt after the chewing gum was spat out.

[Example 21] Candy Scenting Evaluation

[Chem. 35]

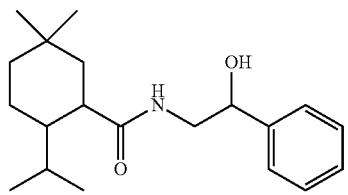

(1-1)

-continued

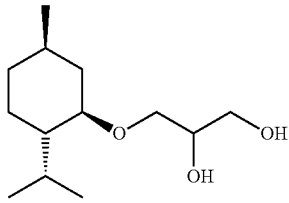
(Comparative Compound 5)

A sensory evaluation was performed on a candy that was scented with 1-menthol and the so far known comparative compound 5 ("Coolact (registered trademark) 10" manufactured by Takasago International Corporation), or 1-menthol and the exemplary compound (1-1).

Candies (J) to (L) were prepared according to the following formulations.

(J) candy base 998 g+herb flavor BASE 0.9 g+1-menthol 0.9 g+ethyl alcohol (EtOH) 0.2 g (K) candy base 998 g+herb flavor BASE 0.9 g+1-menthol 0.9 g+comparative compound 5 0.2 g (L) candy base 998 g+herb flavor BASE 0.9 g+1-menthol 0.9 g+exemplary compound (1-1) (10% in EtOH) 0.2 g The prescription for the herb flavor BASE is as follows.

TABLE 7

| (Component) | (Blending Amount g) |
| --- | --- |
| Star anise oil | 0.100 |
| Eucalyptol | 0.276 |
| *Eucalyptus* oil | 0.520 |
| Sage oil | 0.004 |
| Total Amount | 0.900 |

In addition, the prescription for the candy BASE is as follows.

TABLE 8

| (Component) | (Blending Amount g) |
| --- | --- |
| Granulated sugar | 500.0 g |
| Starch syrup (BRIX 85, 47DE) | 430.0 g |
| Purified water | 170.0 g |
| Total Amount | 1100.0 g |

[Method of Preparing Candy]

Granulated sugar, starch syrup, and purified water were mixed and heated to 150° C. Then, the fire was extinguished, dough was weighted, and a flavor and the like were mixed therewith. The mixture flowed to a mold and was molded while the temperature thereof was maintained at 135° C. to 140° C. The mixture was removed from the mold after cooling, and a candy of about 3 g per grain was prepared.

The evaluation was performed by three flavorists. A grain of candy was taken into the mouth and melted by licking, and after the candy was completely disappeared, intensity, persistence, and quality of a cool-feeling in the oral cavity were evaluated.

[Evaluation Comment]

A candy (K) and a candy (L) had a cooling effect stronger than that of a candy (J), and the candy (L) had a cooling effect equal to or stronger than that of the candy (K) even though the blending amount of the cooling agent in the candy (L) was 1/10 of that of the candy (K). Further, the candy (L) exhibited a sharp and clear refresh-feeling at first, and after a while the refresh-feeling became a refresh-feeling that stimulates the back of the throat. Miscellaneous tastes were not felt. In addition, a cooling effect of 30 minutes or longer was felt after the candy was spat out.

[Example 22] Shampoo Scenting Evaluation

[Chem. 36]

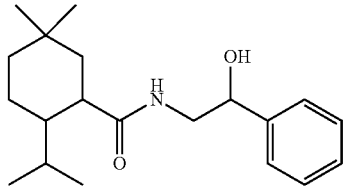
(1-1)

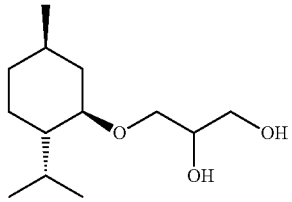
(Comparative Compound 5)

A sensory evaluation was performed on a shampoo that was scented with 1-menthol and the so far known comparative compound 5 ("Coolact (registered trademark) 10" manufactured by Takasago International Corporation), or 1-menthol and the exemplary compound (1-1).

Shampoos (M) to (O) were prepared according to the following formulations.

(M) body-shampoo BASE 900 g+1-menthol 30 g+dipropylene glycol (DPG) 70 g (N) body-shampoo BASE 900 g+1-menthol 30 g+comparative compound 5 (10% in DPG) 70 g (O) body-shampoo BASE 900 g+1-menthol 30 g+exemplary compound (1-1) (1% in DPG) 70 g The prescription for the body-shampoo BASE is as follows.

TABLE 9

| (Component) | (Blending Amount g) |
| --- | --- |
| Aldehyde C-12 Lauric | 0.1 |
| Ambrettolide | 10 |
| Ambroxan | 7.0 |
| Benz acetate | 3.5 |
| Bergamot oil | 30 |
| Canthoxal | 13 |
| Citronellol | 5.5 |
| Cassis base | 10 |
| α-damascones | 1.0 |
| γ-decalactone | 3.0 |
| Dimethyl benzene carbinol | 13 |
| Dipropylene glycol | 63.9 |
| Ethyl linalool | 35 |
| Floralozone | 0.6 |
| Phlorol | 5.0 |
| Grapefruit oil | 40 |
| Galactolipid 50% DPG solution | 55 |
| Hedione | 240 |
| Heliobouquet | 17 |
| 3-cis-hexenyl acetate | 1.5 |
| 3-cis-hexenyl salicylate | 13 |

TABLE 9-continued

| (Component) | (Blending Amount g) |
|---|---|
| 3-cis-hexene-1-ol | 2.5 |
| California lemon oil | 110 |
| Lillial | 70 |
| Manzanate | 0.2 |
| γ-methylionone | 4.0 |
| Methyl pamplemousse | 5.0 |
| Orbiton/Iso-E-super | 100 |
| Phenoxanol | 15 |
| Salicyl acetate | 1.0 |
| Veltol plus | 0.2 |
| Verdox | 25 |
| Total Amount | 900 |

The evaluation was performed by five monitors including male and female monitors. A male monitor and a female monitor washed the hair with about 3 mL of shampoos and about 9 mL of shampoos, respectively, and intensity and persistence of a cool-feeling after the shampoos were washed away were evaluated.

[Evaluation Comment]

A shampoo (N) and a shampoo (O) had a cooling effect stronger than that of a shampoo (M), and the shampoo (O) had a cooling effect equal to or stronger than that of the shampoo (N) even though the blending amount of the cooling agent in the shampoo (O) was 1/10 of that of the shampoo (N).

[Example 23] Beer-Flavored Drink Scenting Evaluation

[Chem. 37]

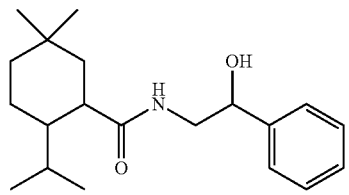

(1-1)

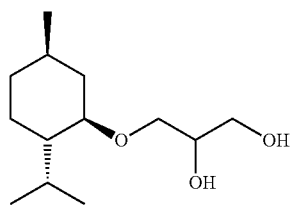

(Comparative Compound 5)

Beer-flavored drinks (P) to (R) that were scented with 1-menthol and the so far known comparative compound 5 ("Coolact (registered trademark) 10" manufactured by Takasago International Corporation), or 1-menthol and the exemplary compound (1-1) separately, were prepared, and the sensory evaluation was performed. The formulations of the beer-flavored drinks (P) to (R) are shown below.

(P) non-alcohol beer taste drink 1000 g+1-menthol 1 mg (1 ppm)

(Q) non-alcohol beer taste drink 1000 g+I-menthol 1 mg (I ppm)+addition of comparative compound 5 1 mg (1 ppm)

(R) non-alcohol beer taste drink 1000 g+1-menthol 1 mg (1 ppm)+addition of exemplary compound (1-1) 0.1 mg (0.1 ppm)

The prescription for the non-alcohol beer taste drink is as follows.

TABLE 10

| (Component) | (Blending Amount g) |
|---|---|
| Reduced maltose starch syrup | 23 |
| Malt extract | 5.0 |
| Indigestible dextrin | 3.0 |
| Anhydrous citric acid | 0.6 |
| Sodium citrate | 0.3 |
| Caramel coloring | 0.2 |
| Vitamin C | 0.05 |
| Isoalpha acid | 0.1 |
| Beer flavor | 1.0 |
| Carbonated water | 966.75 |
| Total Amount | 1000 |

The prescription for the beer flavor contained in the non-alcohol beer taste drink is as follows.

TABLE 11

| (Component) | (Blending Amount g) |
|---|---|
| Ethyl acetate | 50 |
| Isoamyl alcohol | 50 |
| 2-phenylethyl alcohol | 20 |
| Octanoic acid | 8.0 |
| Hexanoic acid | 3.0 |
| Decanoic acid | 0.5 |
| Isoamyl acetate | 2.0 |
| 2-phenylethyl acetate | 2.0 |
| Methionol | 1.0 |
| Ethyl octanoate | 0.5 |
| Ethyl Hexanoate | 0.1 |
| Ethyl decanoate | 0.05 |
| 4-vinyl guaiacol | 0.2 |
| γ-nonalactone | 0.02 |
| Linalool | 0.01 |
| Sotolon | 0.002 |
| Damasenon | 0.001 |
| Propylene glycol (PG) | 862.617 |
| Total Amount | 1000 |

The evaluation was performed by five adult monitors. About 50 mL of beer-flavored drinks cooled to 2° C. to 6° C. were drank, and the intensity, persistence, and quality of a cool-feeling were evaluated.

[Evaluation Comment]

A beer-flavored drink (Q) and a beer-flavored drink (R) had a cooling effect stronger than that of a beer-flavored drink (P), and the beer-flavored drink (R) had a cooling effect equal to or stronger than that of the beer-flavored drink (Q) even though the blending amount of the cooling agent in the beer-flavored drink (R) was 1/10 of that of the beer-flavored drink (Q). Further, the beer-flavored drink (R) had a good and pleasant cool-feeling, as compared to the beer-flavored drink (Q).

[Example 24] Evaluation of Cool-Feeling Intensity (TRPM8 Activity Evaluation)

It is common that a compound having a cooling effect such as menthol generally induces a cool-feeling by activating melastatin transient receptor potential channel 8 (TRPM8) as a cold stimulation receptor (for example, see J. Neurobiol. (2004), Vol. 61, PP. 3-12). Therefore, in order to evaluate the cool-feeling intensity, $EC_{50}$ values of the exemplary compounds obtained in the Examples in TRPM8 activation actions were evaluated according to the following procedures.

(1) Preparation of Human TRPM8 Stable Expression Cell Line

The full-length human TRPM8 gene was amplified from plasmid RC220615 (manufactured by Origene) using a PCR method. The obtained PCR product was subcloned into pcDNA5/FRT/TO (manufactured by Thermo Fisher Scientific K.K.), and then it was introduced into Flp-In293293 cells (manufactured by Thermo Fisher Scientific K.K.) by using a Flp-InT-REx system (manufactured by Thermo Fisher Scientific K.K.), so that a human TRPM8 stable expression cell line was prepared.

(2) Evaluation of Human TRPM8 Activity

The cultured human TRPM8 stable expression cells were seeded at a ratio of 50,000 cells/well to a poly-D-lysine-coated 96-well microplate (manufactured by Corning Incorporated), 1 μg/mL of doxycycline (manufactured by Takara Bio Inc.) was added thereto, and then the seeded cells were cultured at 37° C. for one night, so that the expression of the human TRPM8 was induced.

The culture solution was replaced with a buffer solution, and then, a fluorescent calcium indicator (Fluo4-AM: manufactured by Dojindo) was added thereto, the cells were incubated at 37° C. for 30 minutes, and they were transferred to a fluorescent microplate reader (FlexStation3: Molecular Devices, LLC.). Exemplary compounds were added in a final concentration range of 0.1 μM to 1000 μM, and the changes in fluorescence having a wavelength of 525 nm when excited at a wavelength of 485 nm were measured at a device temperature of 32° C., so as to calculate $EC_{50}$ values.

$EC_{50}$ values of the exemplary compounds in TRPM8 activation actions were shown in the following table.

TABLE 12

| Exemplary Compound | | $EC_{50}$ value (μM) |
|---|---|---|
| 1-1 | 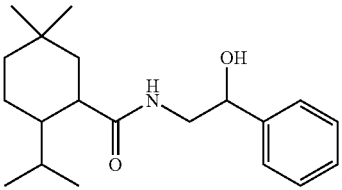 | 0.04099 |
| 1-2 | 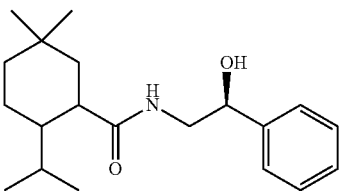 | 0.02409 |
| 1-3 | 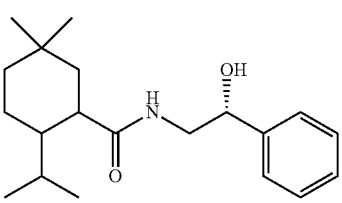 | 0.07359 |
| 1-4 | 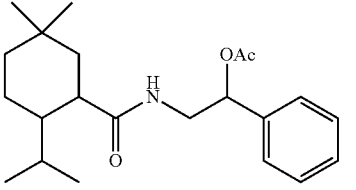 | 0.5413 |
| 1-5 | 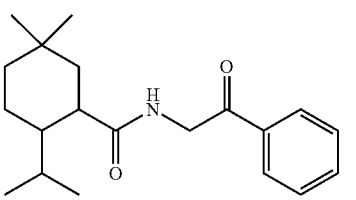 | 0.1489 |
| 1-6 | 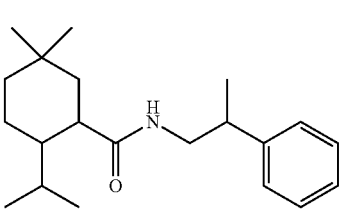 | 0.3877 |
| 1-7 | 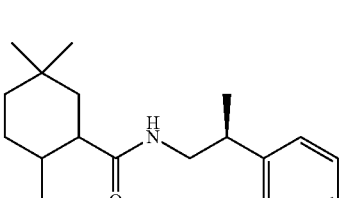 | 0.5545 |
| 1-8 | 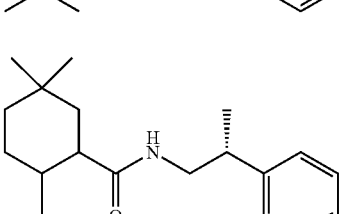 | 0.6104 |
| 1-9 | 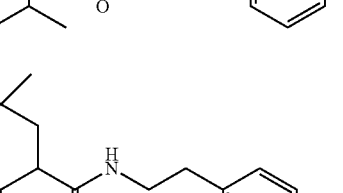 | 0.02975 |
| 1-10 | 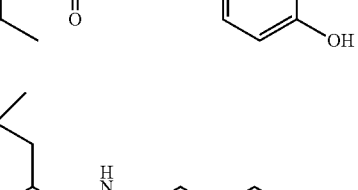 | 0.1580 |

TABLE 12-continued

| Exemplary Compound | EC50 value (μM) |
|---|---|
| 1-11 | 0.1130 |
| 1-12 | 0.4032 |
| 1-13 | 0.05018 |

From the results of Table 12, all of the exemplary compounds (1-1) to (1-13) show low $EC_{50}$ values, suggesting that the exemplary compounds have high cooling effects.

Although the present invention has been described in detail with reference to specific embodiments, it is apparent to those skilled in the art that various changes and modifications can be made without departing from the spirit and scope of the present invention. The present application is based on Japanese Patent Application No. 2017-001852 filed on Jan. 10, 2017, the contents of which are incorporated herein by reference.

The invention claimed is:

1. A cooling agent composition comprising a methyl menthol derivative selected from the group consisting of:

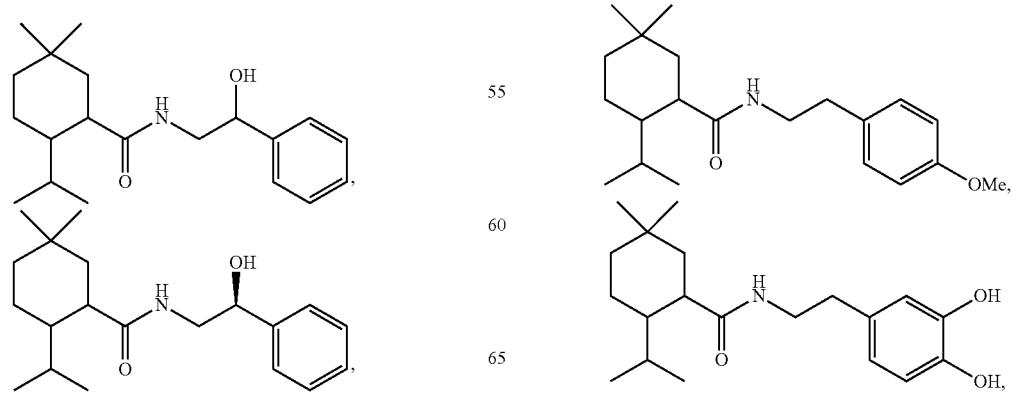

-continued

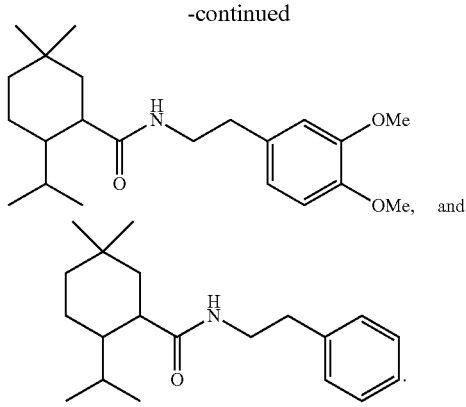

2. The cooling agent composition according to claim 1, wherein the methyl menthol derivative is represented by the following structural formula (2):

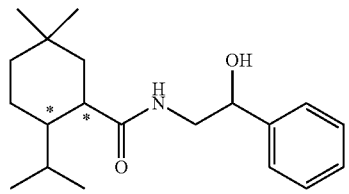

(2)

wherein a symbol * indicates an asymmetric carbon atom.

3. The cooling agent composition according to claim 1, further comprising at least one cooling substance other than the methyl menthol derivative.

4. The cooling agent composition according to claim 3, wherein the cooling substance other than the methyl menthol derivative is at least one cooling substance selected from the group consisting of:

one or more compounds selected from menthol, menthone, camphor, pulegol, isopulegol, cineole, cubenol, menthyl acetate, pulegyl acetate, isopulegyl acetate, menthyl salicylate, pulegyl salicylate, isopulegyl salicylate, 3-(1-menthoxy)propane-1,2-diol, 2-methyl-3-(1-menthoxy)propane-1,2-diol, 2-(1-menthoxy)ethane-1-ol, 3-(1-menthoxy)propane-1-ol, 4-(1-menthoxy)butan-1-ol, menthyl 3-hydroxybutanoate, menthyl glyoxylate, p-menthane-3,8-diol, 1-(2-hydroxy-4-methylcyclohexyl)ethanone, menthyl lactate, menthone glycerin ketal, menthyl-2-pyrrolidone-5-carboxylate, monomenthyl succinate, alkali metal salts of monomenthyl succinate, alkaline earth metal salts of monomenthyl succinate, monomenthyl glutarate, alkali metal salts of monomenthyl glutarate, alkaline earth metal salts of monomenthyl glutarate, N-{[5-methyl-2-(1-methylethyl)cyclohexyl]carbonyl}glycine, p-menthane-3-carboxylic acid glycerol ester, menthol propylene glycol carbonate, menthol ethylene glycol carbonate, p-menthane-2,3-diol, 2-isopropyl-N,2,3-trimethylbutanamide, N-ethyl-p-menthane-3-carboxamide, 3-(p-menthane-3-carboxamide) ethyl acetate, N-(4-methoxyphenyl)-p-menthane carboxamide, N-ethyl-2,2-diisopropylbutanamide, N-cyclopropyl-p-menthane carboxamide, N-(4-cyanomethylphenyl)-p-menthanecarboxamide, N-(2-pyridin-2-yl)-3-p-menthane carboxamide, N-(2-hydroxyethyl)-2-isopropyl-2,3-dimethylbutanamide, N-(1,1-dimethyl-2-hydroxyethyl)-2,2-diethylbutanamide, cyclopropanecarboxylic acid (2-isopropyl-5-methylcyclohexyl)amide, N-ethyl-2,2-diisopropylbutanamide, N-[4-(2-amino-2-oxoethyl)phenyl]-p-menthanecarboxamide, 2-[(2-p-menthoxy)ethoxy] ethanol, 2,6-diethyl-5-isopropyl-2-methyltetrahydropyran, trans-4-tert-butylcyclohexanol, N-[4-(cyanomethyl)phenyl]-2-isopropyl-5,5-dimethylcyclohexylcarboxamide, and N-[3-hydroxy-4-methoxyphenyl]-2-isopropyl-5,5-dimethylcyclohexylcarboxamide;

one or more sugar alcohols selected from xylitol, erythritol, dextrose, and sorbitol; and one or more natural products selected from Japanese mint oil, peppermint oil, spearmint oil, and eucalyptus oil.

5. A sensory stimulant composition comprising the cooling agent composition according to claim 1.

6. The sensory stimulant composition according to claim 5, further comprising at least one warming substance.

7. The sensory stimulant composition according to claim 6, wherein the warming substance is at least one warming substance selected from the group consisting of:

one or more compounds selected from vanillyl methyl ether, vanillyl ethyl ether, vanillyl propyl ether, vanillyl isopropyl ether, vanillyl butyl ether, vanillyl amyl ether, vanillyl isoamyl ether, vanillyl hexyl ether, isovanillyl methyl ether, isovanillyl ethyl ether, isovanillyl propyl ether, isovanillyl isopropyl ether, isovanillyl butyl ether, isovanillyl amyl ether, isovanillyl isoamyl ether, isovanillyl hexyl ether, ethyl vanillyl methyl ether, ethyl vanillyl ethyl ether, ethyl vanillyl propyl ether, ethyl vanillyl isopropyl ether, ethyl vanillyl butyl ether, ethyl vanillyl amyl ether, ethyl vanillyl isoamyl ether, ethyl vanillyl hexyl ether, vanillin propylene glycol acetal, isovanillin propylene glycol acetal, ethyl vanillin propylene glycol acetal, vanillyl butyl ether acetate, isovanillyl butyl ether acetate, ethyl vanillyl butyl ether acetate, 4-(1-menthoxymethyl)-2-(3'-methoxy-4'-hydroxyphenyl)-1,3-dioxolane, 4-(1-menthoxymethyl)-2-(3'-hydroxy-4'-methoxyphenyl)-1,3-dioxolane, 4-(1-menthoxymethyl)-2-(3'-ethoxy-4'-hydroxyphenyl)-1,3-dioxolane, capsaicin, dihydrocapsaicin, nordihydrocapsaicin, homodihydrocapsaicin, homocapsaicin, bis-capsaicin, trishomocapsaicin, nornorcapsaicin, norcapsaicin, capsaicinol, vanillyl caprylamide (octylic acid vanillylamide), vanillyl pelargonamide (nonylic acid vanillylamide), vanillyl caproamide (decylic acid vanillylamide), vanillyl undecanamide (undecylic acid vanillylamide), N-trans-feruloyltyramine, N-5-(4-hydroxy-3-methoxyphenyl)-2E,4E-pentadienoylpiperidine, N-trans-feruloylpiperidine, N-5-(4-hydroxy-3-methoxyphenyl)-2E-pentenoylpiperidine, N-5-(4-hydroxyphenyl)-2E,4E-pentadienoylpiperidine, piperine, isopiperine, chavicine, isochavicine, piperamine, piperettine, piperolein B, retrofractamide A, pipercide, guineenside, piperiline, piperamide C5:1 (2E), piperamide C7:1 (6E), piperamide C7:2 (2E,6E), piperamide C9:1 (8E), piperamide C9:2 (2E,8E), piperamide C9:3 (2E,4E,8E), fagaramide, sanshool-I, sanshool-II, hydroxysanshool, sanshoamide, gingerol, shogaol, zingerone, methylgingerol, paradol, spilanthol, chavicine, polygodial (tadeonal), isopolygodial, dihydropolygodial, and tadeon; and one or more natural products selected from capsicum oil, capsicum oleoresin, ginger oleoresin, jambu oleoresin (*Spilanthes oleracea* extract), sansho extract, sanshoamide, black pepper extract, white pepper extract, and polygonum extract.

8. A flavor or fragrance composition comprising the sensory stimulant composition according to claim 5.

9. A product comprising the sensory stimulant composition according to claim 5, the product being any one of products selected from the group consisting of drinks, foods, fragrances or cosmetics, toiletry products, air care products, daily necessities and household goods, oral compositions, hair care products, skin care products, body care products, detergents for clothes, soft finishing agents for clothes, tobacco, quasi-drugs and pharmaceuticals.

10. The product according to claim 9, wherein a content of the sensory stimulant composition is from 0.00001 mass % to 50 mass %.

11. A product comprising the flavor or fragrance composition according to claim 8, the product being any one of products selected from the group consisting of drinks, foods, fragrances or cosmetics, toiletry products, air care products, daily necessities and household goods, oral compositions, hair care products, skin care products, body care products, detergents for clothes, soft finishing agents for clothes, tobacco, quasi-drugs and pharmaceuticals.

12. The product according to claim 11, wherein a content of the flavor or fragrance composition is from 0.00001 mass % to 50 mass %.

13. The flavor or fragrance composition according to claim 8, wherein a content of the sensory stimulant composition is from 0.00001 mass % to 90 mass %.

14. A methyl menthol derivative selected from the group consisting of:

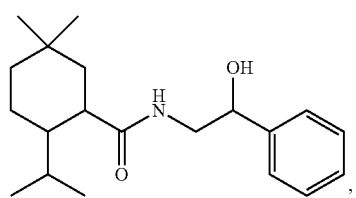
,
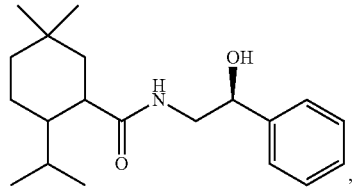
,
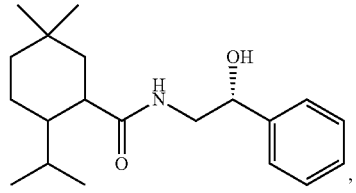
,
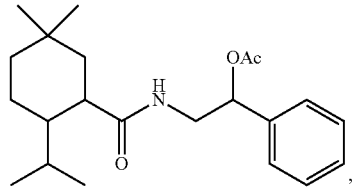
,

-continued

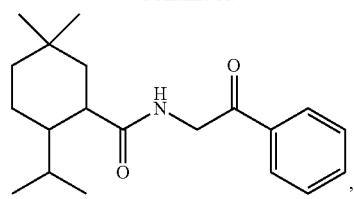
,
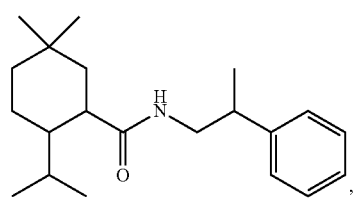
,
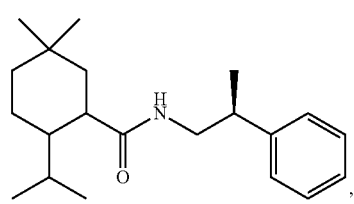
,
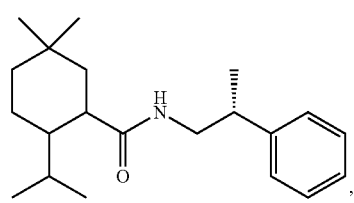
,
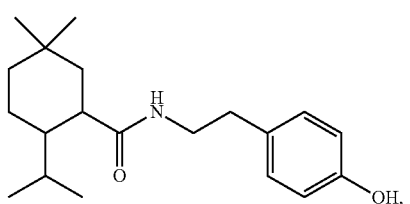
,
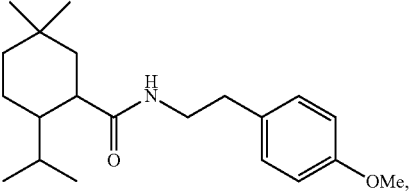
,
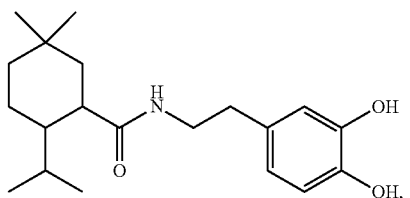
,
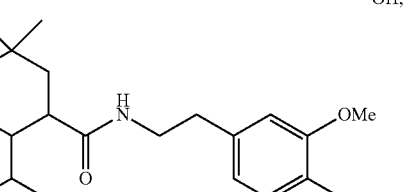
, and -continued

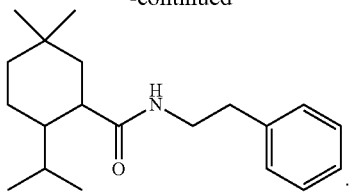

15. The methyl menthol derivative according to claim 14, wherein the methyl menthol derivative is represented by the following structural formula (2):

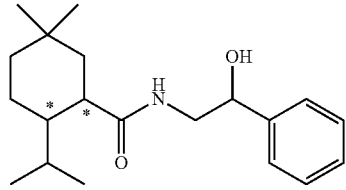

(2)

wherein a symbol * indicates an asymmetric carbon atom.

16. A method of manufacturing a product, comprising blending a product with the sensory stimulant composition according to claim 5, wherein the product is any one of products selected from the group consisting of drinks, foods, fragrances or cosmetics, toiletry products, air care products, daily necessities and household goods, oral compositions, hair care products, skin care products, body care products, detergents for clothes, soft finishing agents for clothes, tobacco, quasi-drugs and pharmaceuticals.

17. A method of manufacturing a product, comprising blending a product with the flavor or fragrance composition according to claim 8, wherein the product is any one of products selected from the group consisting of drinks, foods, fragrances or cosmetics, toiletry products, air care products, daily necessities and household goods, oral compositions, hair care products, skin care products, body care products, detergents for clothes, soft finishing agents for clothes, tobacco, quasi-drugs and pharmaceuticals.

* * * * *